United States Patent [19]
Boyle et al.

[11] Patent Number: 5,789,417
[45] Date of Patent: Aug. 4, 1998

[54] TRICYCLIC COMPOUNDS WITH PHARMACEUTICAL ACTIVITY

[75] Inventors: Francis Thomas Boyle, Congleton; James William Crook, Cheadle; Zbigniew Stanley Matusiak, Holmes Chapel, all of Great Britain

[73] Assignees: Zeneca Limited; British Technology Group Ltd., both of London, United Kingdom

[21] Appl. No.: 432,161

[22] PCT Filed: Nov. 4, 1993

[86] PCT No.: PCT/GB93/02281

§ 371 Date: Jun. 28, 1995

§ 102(e) Date: Jun. 28, 1995

[87] PCT Pub. No.: WO94/11354

PCT Pub. Date: May 26, 1994

[30] Foreign Application Priority Data

Nov. 6, 1992 [GB] United Kingdom ............ 9223352

[51] Int. Cl.⁶ .................... C07D 239/70; A61K 31/495
[52] U.S. Cl. ............................ 514/267; 544/249
[58] Field of Search ............... 544/249; 514/267

[56] References Cited

U.S. PATENT DOCUMENTS

| | | | |
|---|---|---|---|
| 4,447,608 | 5/1984 | Jones et al. | 544/287 |
| 4,564,616 | 1/1986 | Jones et al. | 514/260 |
| 4,925,939 | 5/1990 | Watanabe | 544/251 |
| 4,981,856 | 1/1991 | Hughes | 514/259 |
| 4,992,550 | 2/1991 | Hughes | 544/284 |
| 5,077,404 | 12/1991 | Piper et al. | 544/250 |
| 5,089,499 | 2/1992 | Barker et al. | 514/259 |
| 5,187,167 | 2/1993 | Hughes | 514/259 |
| 5,236,927 | 8/1993 | Jones et al. | 514/259 |
| 5,252,573 | 10/1993 | Barker et al. | 514/259 |
| 5,395,838 | 3/1995 | Barker et al. | 514/211 |

FOREIGN PATENT DOCUMENTS

| | | |
|---|---|---|
| 0409125 | 1/1991 | European Pat. Off. |
| 0438261 | 7/1991 | European Pat. Off. |
| 0509643 | 10/1992 | European Pat. Off. |
| 0562734 | 9/1993 | European Pat. Off. |
| 9113890 | 9/1991 | WIPO |
| 9119700 | 12/1991 | WIPO |
| 9205153 | 4/1992 | WIPO |
| 9205173 | 4/1992 | WIPO |
| 9403439 | 2/1994 | WIPO |

OTHER PUBLICATIONS

Pendergast et al., Benzo [f] quinazoline Inhibitors of Thymidylate Synthase: Methyleneamino-Linked Aroylglutamate Derivatives, J. Med. Chem., 1994, 838–844.

*Primary Examiner*—John M. Ford
*Attorney, Agent, or Firm*—Pillsbury Madison & Sutro, LLP Intellectual Property Group

[57] ABSTRACT

The invention relates to tricyclic compounds of formula (I)

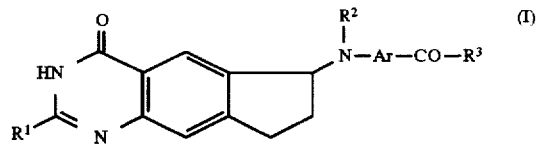

wherein $R^1$ is hydrogen, amino, (1–4C)alkyl, (1–4C)alkoxy, hydroxy-(1–4C)alkyl or fluoro-(1–4C)alkyl; $R^2$ is hydrogen, (1–4C)alkyl, (3–4C)alkenyl, (3–4C)alkynyl, hydroxy-(2–4C)alkyl, halogeno-(2–4C)alkyl or cyano-(1–4C)alkyl; Ar is optionally-substituted phenylene, thiophenediyl, thiazolediyl, pyridinediyl or pyrimidinediyl; and $R^3$ includes a group of the formula —NHCH($CO_2H$)—$A^1$—$Y^1$ wherein $A^1$ is (1–6C)alkylene and $Y^1$ is carboxy, tetrazol-5-yl, N-[(1–4C)alkylsulphonyl]carbamoyl, N(phenylsulphonyl)carbamoyl, tetrazol-5-ylthio, tetrazol-5-ylsulphinyl or tetrazol-5-ylsulphonyl; or pharmaceutically-acceptable salts or esters thereof; to processes for their manufacture; to pharmaceutical compositions containing them; and to their use as anti-cancer agents.

11 Claims, No Drawings

TRICYCLIC COMPOUNDS WITH PHARMACEUTICAL ACTIVITY

This is a §371 National Phase Application of PCT/GB93/02281 filed Nov. 4, 1993.

This invention relates to tricyclic compounds, or pharmaceutically-acceptable salts or esters thereof, which possess anti-cancer activity. The invention includes tricyclic compounds, processes for their manufacture, pharmaceutical compositions containing them and their use in the manufacture of medicaments for use in the production of an anti-cancer effect in a warm-blooded animal such as man.

One group of anti-tumour compounds comprises the antimetabolites, such as aminopterin and methotrexate, which are inhibitors of enzymes which utilise folic acid derivatives. A newer compound of this type which showed considerable promise in clinical trials is known as CB3717 and is described and claimed in United Kingdom Patent Specification No. 2065653B. Despite its promising activity against human breast, ovarian and liver cancer however, CB3717 shows symptoms of toxicity in humans, particularly in relation to the liver and kidney (Cancer Treatment Reports, 1986, 70, 1335).

Compounds of the CB3717-type are believed to act as anti-tumour agents by inhibiting the enzyme thymidylate synthase, which enzyme catalyses the methylation of deoxyuridine monophosphate to produce thymidine monophosphate which is required for DNA synthesis. The anti-cancer activity of CB3717 may be assessed in vitro by determining its inhibitory effect on that enzyme, and in cell cultures by its inhibitory effect on cancer cell lines such as the mouse leukaemia cell line L1210, the mouse lymphoma cell line L5178Y TK-/- and the human breast cancer cell line MCF-7.

Other compounds of the CB3717-type have been described and claimed in European Patent Application Nos. 0 239 362, 0 284 338, 0 339 976, 0 373 891, 0 459 730 and 0 509 643. These compounds and the new compounds of the present invention may have their anti-cancer activity assessed by their activity against, for example, thymidylate synthase and the L1210, L5178Y TK-/- and MCF-7 cell lines.

Antimetabolites, such as aminopterin and methotrexate, which are inhibitors of enzymes which utilise folic acid derivatives, have also shown promise in the treatment of various allergic diseases such as allergic rhinitis, atopic dermatitis and psoriasis. The tricyclic compounds of the present invention, being antimetabolites, are thus of value as therapeutic agents in the treatment of, for example, allergic conditions such as psoriasis.

Antimetabolites such as methotrexate have also shown promise in the treatment of various inflammatory diseases such as inflammation of the joints (especially rheumatoid arthritis, osteoarthritis and gout) and inflammation of the gastrointestinal tract (especially inflammatory bowel disease, ulcerative colitis and gastritis) [*New England J. Med.*, 1985, 312, 818]. The tricyclic compounds of the present invention are thus of value as therapeutic agents in the treatment of, for example, inflammatory disease such as rheumatoid arthritis.

We have now found that the tricyclic compounds of the present invention possess potent inhibitory activity against thymidylate synthase and also potent anti-cancer activity as demonstrated by inhibition of the growth of the L1210, L5178Y TK-/- and MCF-7 cell lines.

According to the invention there is provided a tricyclic compound of the formula I:

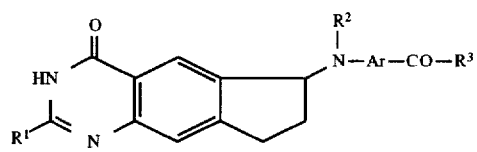

wherein $R^1$ is hydrogen, amino, (1–4C)alkyl, (1–4C)alkoxy, hydroxy-(1–4C)alkyl or fluoro-(1–4C)alkyl;

$R^2$ is hydrogen, (1–4C)alkyl, (3–4C)alkenyl, (3–4C)alkynyl, hydroxy-(2–4C)alkyl, halogeno-(2–4C)alkyl or cyano-(1–4C)alkyl;

Ar is phenylene, thiophenediyl, thiazolediyl, pyridinediyl or pyrimidinediyl which may optionally bear one or two substituents selected from the group consisting of halogeno, hydroxy, amino, nitro, cyano, trifluoromethyl, (1–4C)alkyl and (1–4C)alkoxy; and $R^3$ is a group of the formula

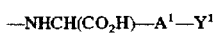
—NHCH(CO₂H)—A¹—Y¹ wherein $A^1$ is (1–6C)alkylene and $Y^1$ is carboxy, tetrazol-5-yl, N-|(1-4C)alkylsulphonyl|carbamoyl, N-(phenylsulphonyl)carbamoyl, tetrazol-5-ylthio, tetrazol-5-ylsulphinyl or tetrazol-5-ylsulphonyl, or $Y^1$ is a group of the formula

—CONH—CH(CO₂H)—A²Y² wherein the α-amino acid carbon atom has the D-configuration, $A^2$ is (1–6C)alkylene and $Y^2$ is carboxy or tetrazol-5-yl, and wherein said N-(phenylsulphonyl) carbamoyl group may optionally bear one or two substituents on the phenyl ring selected from the group consisting of halogeno, nitro, (1–4C)alkyl and (1–4C)alkoxy, or $R^3$ is a N-linked naturally-occurring amino acid selected from the group consisting of L-alanine, L-leucine, L-isoleucine, L-valine and L-phenylalanine, or $R^3$ is a group of the formula

—NH—A³—Y³ wherein $A^3$ is (1–3C)alkylene and $Y^3$ is phenyl which may optionally bear one, two or three substituents selected from the group consisting of halogeno, hydroxy, amino, nitro, cyano, trifluoromethyl, (1–4C)alkyl and (1–4C)alkoxy;

or a pharmaceutically-acceptable salt or ester thereof.

In this specification terms such as alkyl and alkylene include both straight and branched chain groups but references to individual groups such as propyl or trimethylene are specific for the straight chain version only.

It will be observed that the tricyclic compounds of the present invention possess at least one asymmetric carbon atom [at the attachment point of the —N(R)— group to the tricyclic ring] and can therefore exist in racemic and optically active forms. It is to be understood that the present invention encompasses a racemic form of the tricyclic compound of the invention, any optically-active form thereof or a mixture thereof which possesses anti-cancer activity. It is a matter of common general knowledge how such optically-active forms may be obtained by stereospecific synthesis or by the separation of mixtures of isomeric compounds.

It is also to be understood that a tricyclic compound of the formula I may exhibit the phenomenon of tautomerism and that the formulae drawings presented within this specification can represent only one of the possible tautomeric forms. In particular it will be appreciated that when $Y^1$ is a tetrazol-5-yl group, that group may be in the form, for example, of a 1H-tetrazol-5-yl group or a 3H-tetrazol-5-yl group. It is to be understood that the invention encompasses any tautomeric form which possesses anti-cancer activity and is not to be limited merely to any one tautomeric form utilised within the formulae drawings.

It is also to be understood that certain tricyclic compounds of the formula I can exist in solvated as well as unsolvated forms such as, for example, hydrated forms. It is to be understood that the invention encompasses all such solvated forms which possess anti-cancer activity.

Suitable values for the generic radicals referred to above include those set out below.

A suitable value for $R^1$ or $R^2$ when it is (1–4C)alkyl, or for a (1–4C)alkyl substituent which may be present on Ar or on a phenyl-containing group in $R^3$, is, for example, methyl, ethyl, propyl, isopropyl or butyl.

A suitable value for $R^1$ when it is (1–4C)alkoxy, or for a (1–4C)alkoxy substituent which may be present on Ar or on a phenyl-containing group in $R^3$, is, for example, methoxy, ethoxy, propoxy, isopropoxy or butoxy.

A suitable value for a halogeno substituent which may be present on Ar or on a phenyl-containing group in $R^3$, is, for example, fluoro, chloro or bromo.

A suitable value for $R^1$ when it is hydroxy-(1–4C)alkyl is, for example, hydroxymethyl, 1-hydroxyethyl, 2-hydroxyethyl or 3-hydroxypropyl; and when it is fluoro-(1–4C)alkyl is, for example, fluoromethyl, difluoromethyl, trifluoromethyl or 2-fluoroethyl.

A suitable value for $R^2$ when it is (3–4C)alkenyl is, for example, prop-2-enyl, but-2-enyl, but-3-enyl or 2-methylprop-2-enyl: when it is (3–4C)alkynyl is, for example, prop-2-ynyl or but-3-ynyl; when it is hydroxy-(2–4C)alkyl is, for example, 2-hydroxyethyl or 3-hydroxypropyl; when it is halogeno-(2–4C)alkyl is, for example, 2-fluoroethyl, 2-chloroethyl, 2-bromoethyl, 3-fluoropropyl, 3-chloropropyl or 3-bromopropyl; and when it cyano-(1–4C)alkyl is, for example, cyanomethyl, 2-cyanoethyl or 3-cyanopropyl.

A suitable value for Ar when it is phenylene is, for example, 1,3- or 1,4-phenylene, especially 1,4-phenylene.

A suitable value for Ar when it is thiophenediyl is, for example, thiophene-2,4-diyl or thiophene-2,5-diyl; when it is thiazolediyl is, for example, thiazole-2,4-diyl or thiazole-2,5-diyl; when it is pyridinediyl is, for example, pyridine-2,4-diyl, pyridine-2,5-diyl, pyridine-2,6-diyl or pyridine-3,5-diyl; and when it is pyrimidinediyl is, for example, pyrimidine-2,4-diyl, pyrimidine-2,5-diyl or pyrimidine-4,6-diyl.

When $R^3$ is a group of the formula

—NHCH(CO$_2$H)—A$^1$—Y$^1$ then the α-amino acid carbon atom may be racemic or it may have either the L- or D-configuration (preferably the L-configuration), a suitable value for $A^1$ or $A^2$ when it is (1–6C)alkylene is, for example, methylene, ethylene, trimethylene, tetramethylene, pentamethylene or hexamethylene;

and a suitable value for $Y^1$ when it is N-|(1–4C) alkylsulphonyl|carbamoyl is, for example, N-methylsulphonylcarbamoyl, N-ethylsulphonylcarbamoyl or N-propylsulphonylcarbamoyl.

When $R^3$ is a group of the formula

—NH—A$^3$—Y$^3$ then a suitable value for $A^3$ when it is (1–3C)alkylene is, for example, methylene, ethylene, ethylidene or trimethylene.

A suitable pharmaceutically-acceptable salt of a tricyclic compound of the invention which is sufficiently basic is an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a tricyclic compound of the invention which is sufficiently acidic is an alkali metal salt, for example a calcium or magnesium salt, an ammonium or tetra-(2-hydroxyethyl)ammonium salt or a salt with an organic base which affords a physiologically-acceptable cation, for example a salt with methylamine, trimethylamine or tris-(2-hydroxyethyl)amine.

A suitable pharmaceutically-acceptable ester of a tricyclic compound of the invention is, for example, an ester with a (1–6C)alcohol, for example a methyl, ethyl or tert-butyl ester.

Particular novel compounds of the invention are, for example, tricyclic compounds of the formula I as defined in paragraphs (a) to (i) hereinafter and wherein, unless otherwise stated, each of $R^1$, $R^2$, $R^3$ have any of the meanings defined hereinbefore or in this section concerning particular compounds of the invention (a) $R^1$ is hydrogen, amino, methyl or hydroxymethyl;

(b) $R^1$ is methyl;

(c) $R^2$ is hydrogen, methyl, ethyl, propyl, prop-2-enyl, prop-2-ynyl, 2-hydroxyethyl, 2-fluoroethyl, 2-bromoethyl or 2-cyanoethyl;

(d) $R^2$ is prop-2-ynyl;

(e) Ar is 1,4-phenylene which may optionally bear one or two substituents selected from the group consisting of fluoro and chloro, particularly Ar is 1,4-phenylene which bears a 2-fluoro substituent (with the —CO— group in the 1-position);

(f) Ar is thiophene-2,5-diyl or thiazole-2,5-diyl;

(g) Ar is pyridine-2,5-diyl (with the —CO— group in the 2-position);

(h) $R^3$ is a group of the formula

—NHCH(CO$_2$H)—A$^1$—Y$^1$ wherein $A^1$ is methylene, ethylene, trimethylene, tetramethylene or pentamethylene and $Y^1$ is carboxy, tetrazol-5-yl, N - m e t h y l s u l p h o n y l c a r b a m o y l , N-ethylsulphonylcarbamoyl, N-phenylsulphonylcarbamoyl or tetrazol-5-ylthio, or $Y^1$ is a group of the formula

—CONH—CH(CO$_2$H)—A$^2$—Y$^2$ wherein the α-amino acid carbon atom has the D-configuration, $A^2$ is ethylene, trimethylene, tetramethylene or pentamethylene and $Y^2$ is carboxy or tetrazol-5-yl; or (i) $R^3$ is a group of the formula

—NH—A$^3$—Y$^3$ wherein $A^3$ is methylene, ethylene or ethylidene and $Y^3$ is phenyl which may optionally bear one, two or three substituents selected from the group consisting of fluoro, chloro, bromo, nitro, cyano, trifluoromethyl, methyl and methoxy; or a pharmaceutically-acceptable salt or ester thereof.

A preferred compound of the invention is, for example, a tricyclic compound of the formula I wherein $R^1$ is amino or methyl;

$R^2$ is prop-2-ynyl;

Ar is 1,4-phenylene which may optionally bear one or two fluoro or chloro substituents, or Ar is thiophene-2,5-diyl or thiazole-2,5-diyl (with the —CO— group in the 2-position); and $R^3$ is a group of the formula

—NHCH(CO$_2$H)—A$^1$—Y$^1$ wherein $A^1$ is methylene, ethylene, trimethylene, tetramethylene or pentamethylene and $Y^1$ is carboxy, tetrazol-5-yl, N-methylsulphonylcarbamoyl or tetrazol-5-ylthio;

or $R^3$ is a group of the formula

—NH—A$^3$—Y$^3$ wherein $A^3$ is methylene or ethylene and $Y^3$ is phenyl which may optionally bear one or two substituents selected from the group consisting of fluoro, chloro, nitro, cyano and trifluoromethyl; or a pharmaceutically-acceptable salt or ester thereof.

A further preferred compound of the invention is, for example, a tricyclic compound of the formula I wherein $R^1$ is methyl;

$R^2$ is hydrogen, methyl, ethyl, propyl, prop-2-enyl or prop-2-ynyl;

Ar is 1,4-phenylene or 2-fluoro-1,4-phenylene (with the —CO— group in the 1-position), or Ar is pyridine-2, 5-diyl (with the —CO— group in the 2-position); and $R^3$ is a group of the formula

—NHCH(CO$_2$H)—A$^1$—Y$^1$ wherein $A^1$ is ethylene, trimethylene, tetramethylene or pentamethylene and $Y^1$ is carboxy, tetrazol-5-yl, N-methylsulphonylcarbamoyl or tetrazol-5-ylthio;

or a pharmaceutically-acceptable salt or ester thereof.

A further preferred compound of the invention, is for example a tricyclic compound of the formula I wherein $R^1$ is methyl;

$R^2$ is prop-2-ynyl;

Ar is 1,4-phenylene or 2-fluoro-1,4-phenylene (with the —CO— group in the 1-position); and $R^3$ is a group of the formula

—NHCH(CO$_2$H)—A$^1$—Y$^1$ wherein $A^1$ is methylene, ethylene, trimethylene, tetramethylene or pentamethylene and $Y^1$ is carboxy, tetrazol-5-yl, N-methylsulphonylcarbamoyl or tetrazol-5-ylthio; or a pharmaceutically-acceptable salt or ester thereof.

A further preferred compound of the invention is, for example, a tricyclic compound of the formula I wherein $R^1$ is methyl;

$R^2$ is prop-2-ynyl;

Ar is 1,4-phenylene or 2-fluoro-1,4-phenylene (with the —CO— group in the 1-position); and $R^3$ is a group of the formula

—NH—A$^3$—Y$^3$ wherein $A^3$ is methylene and $Y^3$ is phenyl which may optionally bear one substituent selected from the group consisting of fluoro, chloro, nitro, cyano and trifluoromethyl; or a pharmaceutically-acceptable salt thereof.

A further preferred compound of the invention is, for example, a tricyclic compound of the formula I wherein $R^1$ is methyl;

$R^2$ is prop-2-ynyl;

Ar is 1,4-phenylene or 2-fluoro-1,4-phenylene (with the —CO— group in the 1-position), or Ar is pyridine-2, 5-diyl (with the —CO— group in the 2-position); and $R^3$ is a group of the formula

—NHCH(CO$_2$H)—A$^1$—Y$^1$ wherein $A^1$ is ethylene and $Y^1$ is carboxy or tetrazol-5-yl; or a pharmaceutically-acceptable salt or ester thereof.

A specific especially preferred compound of the invention is, for example, the following tricyclic compound of the formula I:

N-{p-[N-((6RS)-2-methyl-4-oxo-3,4,7,8-tetrahydro-6H-cyclopenta[g]quinazolin-6-yl)-N-(prop-2-ynyl)amino] benzoyl}-L-glutamic acid, (2S)-2-{p-[N-((6RS)-2-methyl-4-oxo-3,4,7,8-tetrahydro-6H-cyclopenta-[g]quinazolin-6-yl)-N-(prop-2-ynyl) amino]benzamido}adipic acid, (2S)-2-{p-[N-((6RS)-2-methyl-4-oxo-3,4,7,8-tetrahydro-6H-cyclopenta-[g]quinazolin-6-yl)-N-(prop-2-ynyl) amino]benzamido}pimelic acid, (2S)-2-{p-[N-((6RS)-2-methyl-4-oxo-3,4,7,8-tetrahydro-6H-cyclopenta-[g]quinazolin-6-yl)-N-(prop-2-ynyl) amino]benzamido}-5-[(N-methylsulphonyl)carbamoyl] pentanoic acid, 2-{p-[N-((6S)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyric acid or (2R)-2-{p-[N-((6RS)-2-methyl-4-oxo-3,4,7,8-tetrahydro-6H-cyclopenta-[g]quinazolin-6-yl)-N-(prop-2-ynyl) amino]benzamido}-3-(tetrazol-5-ylthio)propionic acid;

or a pharmaceutically-acceptable salt or ester thereof.

A further specific especially preferred compound of the invention is, for example, the following tricyclic compound of the formula I:

(2S)-2-{p-[N-((6S)-2-methyl-4-oxo-3,4,7,8-tetrahydro-6H-cyclopenta[g]-quinazolin-6-yl)-N-(prop-2-ynyl)amino] benzamido}-4-(tetrazol-5-yl)-butyric acid, (2S)-2-{5-[N-((6RS)-2-methyl-4-oxo-3,4,7,8-tetrahydro-6H-cyclopenta[g]quinazolin-6-yl)-N-(prop-2-ynyl) amino]pyridine-2-carboxamido}-4-(tetrazol-5-yl)butyric acid, (2S)-2-{o-fluoro-p-[N-methyl-N-((6RS)-2-methyl-4-oxo-3, 4,7,8-tetrahydro-6H-cyclopenta[g]quinazolin-6-yl) amino]benzamido}-4-(tetrazol-5-yl)butyric acid, (2S)-2-[o-fluoro-p-[N-((6RS)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyric acid or N-{o-fluoro-p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid;

or a pharmaceutically-acceptable salt or ester thereof.

A further specific especially preferred compound of the invention is, for example, the following tricyclic compound of the formula I:

N-(3-cyanobenzyl)-p-[N-((6RS)-2-methyl-4-oxo-3,4,7,8-tetrahydro-6H-cyclopenta[g]quinazolin-6-yl )-N-(prop-2-ynyl)amino]benzamide;

or a pharmaceutically-acceptable salt thereof.

A further specific especially preferred compound of the invention is, for example, the following tricyclic compound of the formula I:

N-{p-[N-((6S)-2-methyl-4-oxo-3,4,7,8-tetrahydro-6H-cyclopenta-[g]quinazolin-6-yl)-N-(prop-2-ynyl)amino] benzoyl}-L-glutamic acid, N-{o-fluoro-p-[N-((6S)-2-methyl-4-oxo-3,4,7,8-tetrahydro-6H-cyclopenta[g]quinazolin-6-yl)-N-(prop-2-ynyl) amino]benzoyl}-L-glutamic acid, N-{5-|N-((6S)-2-methyl-4-oxo-3,4,7,8-tetrahydro-6H-cyclopenta-|g|quinazolin-6-yl)-N-(prop-2-ynyl)amino| pyridyl-2-carbonyl}-L-glutamic acid, (2S)-2-{o-fluoro-p-|N-((6S)-2-methyl-4-oxo-3,4,7,8-tetrahydro-6H-cyclopenta|g|quinazolin-6-yl)-N-(prop-2-ynyl)amino|benzamido}-4-(tetrazol-5-yl)butyric acid or (2S)-2-{5-|N-((6S)-2-methyl-4-oxo-3,4,7,8-tetrahydro-6H-cyclopenta-|g|quinazolin-6-yl)-N-(prop-2-ynyl)amino| pyridine-2-carboxamido}-4-(tetrazol-5-yl)butyric acid;

or a pharmaceutically-acceptable salt thereof.

A compound of the invention comprising a tricyclic compound of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $R^1$, $R^2$, Ar and $R^3$ have any of the meanings defined hereinbefore, provided that, when there is an amino, hydroxy or carboxy group in $R^1$, $R^2$, Ar or $R^3$, any such group may optionally be protected by a conventional protecting group which may be removed when so desired by conventional means.

(a) The reaction of an acid of the formula II

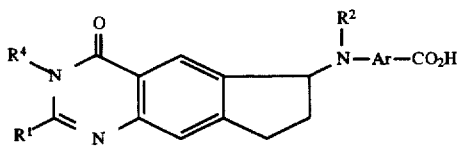

or a reactive derivative thereof, wherein $R^4$ is hydrogen or a protecting group, with the amino group of a compound of the formula $R^3$—H.

A suitable reactive derivative of an acid of the formula II is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo-|5.4.0|undec-7-ene. The reaction is also preferably carried out in a suitable inert solvent or diluent, for example tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, -78° to 150° C., conveniently at or near ambient temperature.

A suitable value for $R^4$ when it is a protecting group is, for example, a pivaloyloxymethyl group which may be removed by hydrolysis with a base, for example sodium hydroxide or ammonia, in a suitable inert solvent or diluent, for example methanol or ethanol.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The starting materials of the formula II and of the formula $R^3$—H may be prepared by standard procedures of organic chemistry. The preparation of examples of such starting materials is described within the accompanying non-limiting Examples which are provided for the purpose of illustration only. Other necessary starting materials are obtainable by analogous procedures to those described or by modifications thereto which are within the ordinary skill of an organic chemist. Thus, for example, the starting material of the formula II may be prepared by the reaction of a compound of the formula III

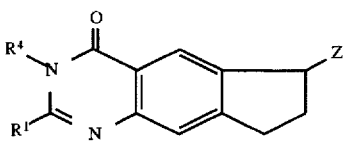

wherein Z is a displaceable group, with an amine of the formula:

HNR²—Ar—CO₂R⁵ wherein $R^5$ is a protecting group which can be removed to provide a carboxylic acid.

A suitable value for the displaceable group Z is, for example, a halogeno or sulphonyloxy group, for example a chloro, bromo, mesyloxy or 4-toluenesulphonyloxy group.

A suitable value for $R^5$ is, for example, an alkyl group such as a methyl or ethyl group which may be removed by hydrolysis with a base such as sodium hydroxide, or $R^5$ is a tert-butyl group which may be removed by cleavage with an acid, for example an organic acid such as trifluoroacetic acid. The protecting group $R^5$ may be, for example, an esterifying group which can be removed while the protecting group for any amino, hydroxy or carboxy group in $R^1$, $R^2$ and Ar is retained.

(b) The reaction of a compound of the formula III wherein $R^4$ is hydrogen or a protecting group as defined above and Z is a displaceable group as defined above, with an amine of the formula:

HNR²—Ar—CO—R³

The reaction is preferably carried out in the presence of a suitable base as defined above, in a suitable inert solvent or diluent as defined above, and at a temperature in the range, for example, 25° to 150° C., conveniently at or near 90° C.

The starting materials of the formula III and of the formula:

HNR²—Ar—CO—R³ may be prepared by standard procedures of organic chemistry. The preparation of examples of compounds of the formula III is described within the accompanying non-limiting Examples which are provided for the purpose of illustration only. Other necessary starting materials are obtainable by analogous procedures to those described or by modifications thereto which are within the ordinary skill of an organic chemist.

(c) The alkylation of an amine of the formula IV

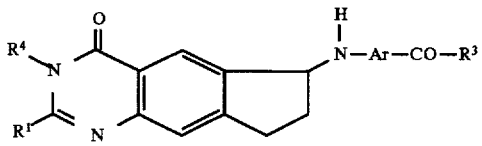

wherein $R^4$ is hydrogen or a protecting group as defined above, with an alkylating agent of the formula R²—Z where Z is a displaceable group as defined above.

The reaction is preferably carried out in the presence of a suitable base as defined above, in a suitable inert solvent or diluent as defined above, and at a temperature in the range, for example, 25° to 150° C., conveniently at or near 100° C.

The preparation of examples of amines of the formula IV is described within the accompanying non-limiting Examples which are provided for the purpose of illustration only. Other necessary starting materials are obtainable by procedures within the ordinary skill of an organic chemist.

(d) The reductive amination of a compound of the formula R²'—CHO, wherein R²' is defined such that R²'—CH₂ has any of the meanings defined above for R², with an amine of the formula IV.

The reaction is performed in the presence of a suitable reducing agent, for example an alkali metal borohydride or cyanoborohydride such as sodium cyanoborohydride, in the presence of a suitable inert solvent or diluent, for example methanol, ethanol or acetic acid, and at a temperature in the range, for example, 10° to 60° C., conveniently at or near ambient temperature.

When a pharmaceutically-acceptable salt of a compound of the formula I is required, it may be obtained, for example, by reaction of said compound with a suitable acid or base using a conventional procedure. When a pharmaceutically-acceptable ester of a compound of the formula I is required it may be obtained, for example, by reaction of said compound with a (1–6C)alcohol using a conventional procedure. When an optically active form of a compound of the formula I is required, it may be obtained by carrying out one of the aforesaid processes using an optically active starting material, or by resolution of a racemic form of said compound using a conventional procedure.

As stated above a tricyclic compound of the present invention possesses anti-cancer activity. This activity may be assessed, for example, using one or more of the procedures set out below:

(a) An in vitro assay which determines the ability of a test compound to inhibit the enzyme thymidylate synthase. Thymidylate synthase was obtained in partially purified form from L1210 mouse leukaemia cells and utilised using the procedures described by Jackman et al. (*Cancer Res.*, 1986, 46, 2810 and Sikora et al., *Biochem. Pharmacol.* 1988, 37 4047);

(b) An assay which determines the ability of a test compound to inhibit the growth of the leukaemia cell line L1210 in cell culture. The test is similar to that described in UK Patent Specification No. 2065653B and has been described by Jones et al., *J. Med. Chem.*, 1985, 28, 1468;

(c) An assay which determines the ability of a test compound to inhibit the growth of the human breast cancer cell line MCF-7 in cell culture. The test is similar to that described by Lippman et al. (*Cancer Res.*, 1976, 36, 4595) and (d) An assay which determines the ability of a test compound to be cytotoxic to the lymphoma cell line L5178Y TK-/- in vitro. The lymphoma cell line L5178Y TK-/- is deficient in the enzyme thymidine kinase with phosphorylates thymidine and thus operates to generate a pool of thymidylate when de novo synthesis of thymidylate is prevented by the presence of an effective amount of an inhibitor of thymidylate synthase. The L5178Y TK-/- cell line is thereby more sensitive to the presence of an inhibitor of thymidylate synthase. [L5178Y TK-/- was obtained by mutation of the parent L5178Y cell line which is described by, for example, Fischer et al., *Methods in Medical Research*, 1964, 10, 247].

Although the pharmacological properties of the tricyclic compounds of the invention vary with structural changes, in general tricyclic compounds of the invention possess activity in one or more of the above tests (a) to (c):

Test (a) IC₅₀ in the range, for example, 0.001–1 μM;
Test (b) IC₅₀ in the range, for example, 0.01–5 μM;
Test (c) IC₅₀ in the range, for example, 0.01–5 μM;
Test (d) IC₅₀ in the range, for example, 0.005–5 μM.

Thus, by way of example, the compound N-{p-[N-((6RS) 2-methyl-4-oxo-3,4,7,8-tetrahydro-6H-cyclopenta[g]

quinazolin-6-yl)-N-(prop-2-ynyl)amino]benzoyl}-L-glutamic acid has an $IC_{50}$ of 0.007 μM in Test (a), an $IC_{50}$ of 0.28 μM in Test (b), an $IC_{50}$ of 0.02 μM in Test (c) and an $IC_{50}$ of 0.72 μM in Test (d).

A tricyclic compound of the present invention may itself be active or it may be a pro-drug which is converted in vivo to an active compound.

A tricyclic compound of the invention, or a pharmaceutically-acceptable salt or ester thereof, may be administered to a warm-blooded animal, including a human, in the form of a pharmaceutical composition which comprises the tricyclic compound, or a pharmaceutically-acceptable salt or ester thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution, emulsion or suspension. In general the above compositions may be prepared in a conventional manner using conventional excipients.

The composition may contain, in addition to the tricyclic compound of the invention, one or more other anti-tumour substances, for example those selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide; and biological response modifiers, for example interferon.

The tricyclic compound will normally be administered to a warm-blooded animal at a unit dose within the range 50–5000 mg per square meter body area of the animal, i.e. approximately 1–100 mg/kg, and this normally provides a therapeutically-effective dose. A unit dose form such as a tablet or capsule will usually contain, for example, 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further feature of the invention there is provided a tricyclic compound of the formula I, or a pharmaceutically-acceptable salt or ester thereof, for use in a method of treatment of the human or animal body by therapy.

According to a further feature of the present invention there is provided a method for producing an anti-cancer effect in a warm-blooded animal, such as man, in need of such treatment which comprises administering to said animal an effective amount of a tricyclic compound of the present invention, or a pharmaceutically-acceptable salt or ester thereof.

The invention also provides the use of a tricyclic compound of the present invention, or a pharmaceutically-acceptable salt or ester thereof, in the manufacture of a novel medicament for use in the production of an anti-cancer effect in a warm blooded animal, such as man.

A tricyclic compound of the present invention is expected to possess a wide range of anti-cancer activities. CB3717 showed promising activity against human breast, ovarian and liver cancer and consequently it is expected that a tricyclic compound of the present invention will possess such anti-cancer activity. It is in addition expected that a compound of the present invention will possess anti-tumour activity against a range of leukaemias, lymphoid malignancies and solid tumours such as carcinomas and sarcomas. The growth of such tumours is mediated by a requirement for the thymidine monophosphate which is produced by the action of thymidylate synthase on deoxyuridine monophosphate. Thymidine monophosphate is one of the essential nucleotides for the synthesis of cellular DNA. In the presence of an effective amount of a thymidylate synthase inhibitor such as an effective amount of a compound of the present invention it is expected that the growth of thymidylate synthase dependent tumours will be inhibited.

As previously mentioned a tricyclic compound of the invention, or a pharmaceutically-acceptable salt or ester thereof, is also of value in the treatment of, for example, allergic conditions such as psoriasis or, for example, inflammatory disease such as rheumatoid arthritis. In using a compound of the invention for such a purpose the compound will normally be administered at a dose within the range 5–500 mg per square meter body area of the animal. In general for the treatment of an allergic condition such as psoriasis topical administration of a tricyclic compound of the invention is preferred. Thus, for example, for topical administration a daily dose in the range, for example, 0.1 to 5 mg/kg will be used.

The invention is illustrated but not limited by the following Examples in which unless otherwise stated:

(i) evaporations were carried out by rotary evaporation in vacuo and work-up procedures were carried out after removal of residual solids by filtration;

(ii) operations were carried out at ambient temperature, that is in the range 18°–20° C. and under an atmosphere of an inert gas such as argon;

(iii) column chromatography (by the flash procedure) and medium pressure liquid chromatography (MPLC) were preformed on Merck Kieselgel silica (Art. 9385) or Merck Lichroprep RP-18 reversed-phase silica (Art. 9303) obtained from E. Merck, Darmstadt, Germany;

(iv) yields are given for illustration only and are not necessarily the maximum attainable;

(v) the end-products of the formula I have satisfactory microanalyses and their structures were confirmed by NMR and mass spectral techniques [proton magnetic resonance spectra were determined using a Jeol FX 90Q or a Bruker AM200 spectrometer operating at a field strength of 200 MHz; chemical shifts are reported in parts per million downfield from tetramethylsilane as an internal standard (δ scale) and peak multiplicities are shown thus: s, singlet; d, doublet; d of d's, doublet of doublet's; t, triplet, m, multiplet; fast-atom bombardment (FAB) mass spectral data were obtained using a VG Analytical MS9 spectrometer and xenon gas and, where appropriate, either positive ion data or negative ion data were collected];

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus, a Koffler hot plate apparatus or an oil-bath apparatus; and (viii) the following abbreviations have been used:
THF tetrahydrofuran;
DMF N,N-dimethylformamide;
DMA N,N-dimethylacetamide;
DMSO dimethylsulphoxide;
NMP N-methylpyrrolidin-2-one.

EXAMPLE 1

A mixture of diethyl N-{p-[N-((6RS)-2-methyl-4-oxo-3-pivaloyloxymethyl-3,4,7,8-tetrahydro-6H-cyclopenta[g]quinazolin-6-yl)amino]benzoyl}-L-glutamate (13.5 g), propargyl bromide (32 g), calcium carbonate (10.7 g) and DMA (250 ml) was stirred and heated to 110° C. for 5 hours. The mixture was evaporated and the residue was partitioned between ethyl acetate and water. The organic phase was washed with water, dried (MgSO$_4$) and evaporated. The residue was purified by column chromatography using increasingly polar mixtures of hexane and ethyl acetate as eluent. There was thus obtained diethyl N-{p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoyl}-L-glutamate as a foam (9 g).

A mixture of the material so obtained, 1N aqueous sodium hydroxide (60 ml) and methanol (300 ml) was stirred at ambient temperature for 24 hours. The mixture was concentrated by evaporation to a volume of approximately 20 ml. Water (200 ml) was added and the mixture was acidified to pH4 by the addition of 2N aqueous hydrochloric acid. The precipitate was isolated, washed with water and dried under vacuum. There was thus obtained N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid (7 g), m.p. 188° C.;

NMR Spectrum: (CD$_3$SOCD$_3$) 2.0 (m, 2H), 2.2 (m, 2H), 2.35 (m, 5H), 3.05 (s, 1H), 3.1 (m, 2H), 3.35 (m, 1H), 4.05 (m, 1H), 4.35 (q, 1H), 5.75 (t, 3H), 7.0 (d, 2H), 7.5 (s, 1H), 7.75 (d, 2H), 7.8 (s, 1H), 8.1 (d, 1H), 12.0 (s, 1H);

Elemental Analysis: Found C, 60.5; H, 5.2; N, 10.5; C$_{27}$H$_{26}$N$_4$O$_6$ 1H$_2$O 0.25 NaCl requires C, 60.6; H, 5.2; N, 10.5%.

The diethyl N-{p-[N-((6RS)-2-methyl-4-oxo-3-pivaloyloxymethyl-3,4,7,8-tetrahydro-6H-cyclopenta[g]quinazolin-6-ylamino]benzoyl}-L-glutamate used as a starting material was obtained as follows:

A mixture of 5-aminoindan (100 g), acetic anhydride (84 g), pyridine (65 g) and ethyl acetate (500 ml) was stirred at ambient temperature for 16 hours. The mixture was evaporated and the residue was triturated under diethyl ether (800 ml). The solid was filtered off, washed with diethyl ether (500 ml) and with hexane (500 ml) and dried. There was thus obtained 5-acetamidoindan (104.5 g), m.p. 107° C.

Bromine (105 g) was added dropwise to a stirred mixture of 5-acetamidoindan (104.5 g) and acetic acid (400 ml), the rate of addition being such that the temperature of the reaction mixture was maintained in the range 20° to 25° C. The mixture was poured into a mixture (2 L) of ice and water. The precipitate was isolated, washed with water and dried. There was thus obtained 5-acetamido-6-bromoindan (143 g), m.p. 138° C.

A mixture of the material so obtained, cuprous cyanide (65.5 g) and NMP (600 ml) was stirred and heated to 125° C. for 30 minutes. The mixture was cooled to ambient temperature and poured into a mixture of concentrated aqueous ammonia solution (specific gravity 0.88, 1 L) and ice (3 L). The mixture was stirred for 15 minutes. The precipitate was isolated and washed with water (3 L). A mixture of the solid so obtained and methylene chloride (2 L) was stirred at ambient temperature for 30 minutes. The mixture was filtered and the filtrate was dried (MgSO$_4$) and evaporated. The residue was triturated under diethyl ether (1.5 L). There was thus obtained 5-acetamido-6-cyanoindan (104 g), m.p. 172° C.

A mixture of the material so obtained, hydrogen peroxide (30% solution in water, 400 ml), sodium hydroxide (35 g), water (200 ml) and ethanol (1 L) was stirred and heated to 50° C. for 1 hour. The mixture was cooled to ambient temperature and evaporated. The residue was dissolved in water (2 L) and the solution was acidified to pH5 by the addition of 2N aqueous hydrochloric acid. The precipitate was isolated, washed with water and dried under vacuum. There was thus obtained 2-methyl-3,4,7,8-tetrahydro-6H-cyclopenta[g]quinazolin-4-one (100 g), m.p. 284° C.

Potassium tert-butoxide (64 g) was added portionwise during 15 minutes to a stirred solution of 2-methyl-3,4,7,8-tetrahydro-6H-cyclopenta[g]quinazolin-4-one (89 g) in DMSO (700 ml). The mixture was stirred at ambient temperature for 30 minutes. Chloromethyl pivaloate (131 g) was added dropwise during 30 minutes. The mixture was stirred at ambient temperature for 24 hours. The mixture was poured into a mixture of ammonium chloride (500 g) and a mixture (3 L) of ice and water. Ethyl acetate (2 L) was added and the mixture was filtered. The organic layer was dried (MgSO$_4$) and evaporated. The residue was triturated under diethyl ether (500 ml). The mixture was cooled to 0° C. for 2 hours. The solid was isolated, washed with diethyl ether and dried. There was thus obtained 2-methyl-3-pivaloyloxymethyl-3,4,7,8-tetrahydro-6H-cyclopenta[g]quinazolin-4-one (72.4 g), m.p. 128° C.

A mixture of a portion (50 g) of the material so obtained, N-bromosuccinimide (31.2 g), benzoyl peroxide (0.1 g) and carbon tetrachloride (500 ml) was stirred and heated to reflux for 90 minutes. The mixture was cooled to 0° C. The mixture was filtered and the filtrate was evaporated. The residue was triturated under diethyl ether (400 ml). The mixture was cooled to 0° C. The precipitate was isolated, washed with diethyl ether and dried. The solid so obtained was purified by column chromatography using a 1:1 mixture of hexane and ethyl acetate as eluent. There was thus obtained 6-bromo-2-methyl-3-pivaloyloxymethyl-3,4,7,8-tetrahydro-6H-cyclopenta[g]quinazolin-4-one (21 g), m.p. 98° C. (decomposes);

NMR Spectrum: 1.2 (s, 9H), 2.55 (m, 2H), 2.65 (s, 3H), 3.0 (m, 1H), 3.3 (m, 1H), 5.65 (d of d's, 1H), 6.1 (q, 2H), 7.5 (s, 1H), 8.3 (s, 1H).

A mixture of the material so obtained diethyl p-aminobenzoyl-L-glutamate (*J. Med. Chem.*, 1985, 28, 1428; 52.5 g), calcium carbonate (27.5 g) and DMA (200 ml) was stirred and heated to 110° C. for 30 minutes. The mixture was cooled to ambient temperature. The mixture was evaporated and the residue was partitioned between ethyl acetate and water. The organic phase was dried (MgSO$_4$) and evaporated. The residue was purified by column chromatography using initially a 1:1 mixture of hexane and ethyl acetate as eluent and then a 1:3 mixture of hexane and ethyl acetate as eluent. There was thus obtained a gum which on trituration under diethyl ether gave diethyl N-{p-[N-((6RS)-2-methyl-4-oxo-3-pivaloyloxymethyl-3,4, 7,8-tetrahydro-6h-cyclopenta[g]quinazolin-6-yl)amino]
benzoyl}-L-glutamate (13.5 g), m.p. 156° C.;

NMR Spectrum: (CD₃SOCD₃) 1.13 (s, 9H), 1.2 (2 t's, 6H), 2.0 (m, 3H), 2.45 (t, 2H), 2.6 (s, 3H), 3.05 (m, 2H1), 4.05 (2 q's, 4H), 4.4 (m, 1H), 5.2 (broad t, 1H), 6.05 (q, 2H), 6.65 (broad s, 1H), 6.8 (d, 2H), 7.5 (s, 1H), 7.7 (d, 2H), 7.95 (s, 1H), 8.25 (d, 1H).

EXAMPLE 2

A mixture of N-{p-[N-((6RS)-2-methyl-4-oxo-3,4,7,8-tetrahydro-6H-cyclopenta[g]quinazolin-6-yl)-N-(prop-2-ynyl)-amino]benzoyl}-L-glutamic acid (5.5 g), carboxypeptidase G₂ (*J. Med. Chem.*, 1992, 35, 859; *Eur. J. Biochem.*, 1985, 148, 447; 2000 units) and tris buffer [prepared by mixing 2-amino-2-hydroxy-methyl-1,3-propanediol (12.11 g), zinc chloride (0.035 g) and distilled water (950 ml), by adjusting the basicity of the mixture to pH7.3 by the addition of 2N aqueous hydrochloric acid and by adding sufficient distilled water to give a final volume of 1 L; 700 ml] was stirred and heated to 37° C. for 2.75 hours. The mixture was cooled to 0° C. and acidified to pH4 by the addition of glacial acetic acid. The precipitate was isolated and dried. The precipitate was purified by column chromatography using initially a 9:1 mixture of methylene chloride and methanol and then a 9:1:0.1 mixture of methylene chloride, methanol and acetic acid as eluent. There were thus obtained:

N-{p-[N-((6S)-2-methyl-4-oxo-3,4,7,8-tetrahydro-6H-cyclopenta[g]quinazolin-6-yl)-N-(prop-2-ynyl)amino] benzoyl}-L-glutamic acid (2.7 g), m.p. 218° C.;

NMR Spectrum: (CD₃SOCD₃) 2.0 (m, 2H), 2.2 (m, 2H), 2.35 (m, 5H), 3.05 (s, 1H), 3.1 (m, 2H), 3.35 (m, 1H), 4.05 (m, 1H), 4.35 (q, 1H), 5.75 (t, 3H), 7.0 (d, 2H), 7.5 (s, 1H), 7.75 (d, 2H), 7.8 (s, 1H), 8.1 (d, 1H), 12.0 (s, 1H);

and p-[N-((6R)-2-methyl-4-oxo-3,4,7,8-tetrahydro-6H-cyclopenta[g]quinazolin-6-yl)-N-(prop-2-ynyl)amino] benzoic acid (2.0 g);

NMR Spectrum: (CD₃SOCD₃) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (s, 1H), 7.85 (d, 2H), 12.1 (broad s, 2H).

EXAMPLE 3

A solution of p-[N-((6S)-2-methyl-4-oxo-3,4,7,8-tetrahydro-6H-cyclopenta[g]quinazolin-6-yl)-N-(prop-2-ynyl)amino]benzoic acid (0.7 g) in DMA (25 ml) was added to a stirred mixture of pentafluorophenol (1.2 g), N,N-dicyclohexylcarbodiimide (0.45 g) and DMA (50 ml). The resultant mixture was stirred at 50° C. for 18 hours. The mixture was evaporated and the residue was purified by column chromatography using initially a 40:1 and then a 20:1 mixture of methylene chloride and methanol as eluent. There was thus obtained pentafluorophenyl p-[N-((6S)-2-methyl-4-oxo-3,4,7,8-tetrahydro)-6H-cyclopenta[g] quinazolin-6-yl)-N-(prop-2-ynyl)amino]benzoate as a solid (0.57 g);

NMR Spectrum: (CD₃SOCD₃) 2.2 (m, 2H), 2.35 (s, 3H), 3.05 (m, 2H), 3.2 (s, 1H), 3.95 (m, 1H), 4.2 (m, 1H), 5.9 (t, 1H), 7.05 (d, 2H), 7.5 (s, 1H), 7.8 (s, 1H), 8.05 (d, 2H).

A mixture of the benzoate so obtained, methyl 2-amino-4-(tetrazol-5-yl)butyrate (0.391 g), N-hydroxybenzotriazole (0.01 g) and DMF (30 ml) was stirred at ambient temperature for 24 hours. The mixture was evaporated and the residue was partitioned between ethyl acetate and water. The organic phase was washed with water, dried (MgSO₄) and evaporated. The residue was purified by column chromatography using initially a 19:1 mixture and then a 9:1 mixture of methylene chloride and methanol as eluent. There was thus obtained methyl 2-{p-[N-((6S)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyrate as a gum (0.52 g).

A mixture of the butyrate so obtained, 1N aqueous sodium hydroxide solution (8 ml) and methanol (40 ml) was stirred at ambient temperature for 18 hours. The mixture was concentrated by evaporation to a volume by approximately 5 ml. Water (25 ml) was added and the mixture was acidified to pH4 by the addition of 2N aqueous hydrochloric acid. The precipitate was isolated, washed with water and dried under vacuum. There was thus obtained 2-{p-[N-((6S)-2-methyl-4-oxo-3,4,7,8-tetrahydro-6H-cyclopenta[g]quinazolin-6-yl)-N-(prop-2-ynyl)amino]benzamido}-4-(tetrazol-5-yl) butyric acid (0.405 g), m.p. 216° C.;

NMR Spectrum: (CD₃SOCD₃) 2.25 (m, 4H), 2.35 (s, 3H), 3.0 (m, 3H), 3.1 (s, 1H), 3.2 (m, 1H), 3.85 (m, 1H), 4.1 (m, 1H), 4.5 (q, 1H), 5.75 (t, 1H), 7.0 (d, 2H), 7.5 (s, 1H), 7.8 (s, 1H), 7.85 (d, 1H), 8.4 (d, 1H), 12.0 (s, 1H), 12.6 (s, 1H), 13.0 (s, 1H);

Elemental Analysis: Found C, 51.1; H, 4.6; N, 17.5; C₂₇H₂₆N₈O₄ 1.25H₂O 1.5 NaCl requires C, 50.9; H, 4.5; N, 17.6%.

In this example the methyl 2-amino-4-(tetrazol-5-yl) butyrate was enriched in the form having the (S)-configuration at the carbon atom which bears the methoxycarbonyl group to the extent that the ratio of (S):(R) form was 7:3 as determined by chromatographic analysis. This isomeric ratio was retained in the product of Example 3.

The p-[N-((6S)-2-methyl-4-oxo-3,4,7,8-tetrahydro-6H-cyclopenta[g]quinazolin-6-yl)-N-(prop-2-ynyl)amino] benzoic acid used as a starting material was obtained as follows:

A mixture of N-{p-[N-((6S)-2-methyl-4-oxo-3,4,7,8-tetrahydro-6H-cyclopenta[g]quinazolin-6-yl)-N-(prop-2-ynyl)amino}-L-glutamic acid (1 g), carboxypeptidase G₂ (1000 units) and tris buffer (200 ml) was stirred and heated to 37° C. for 24 hours. A second portion of carboxypeptidase G₂ (1000 units) was added and the mixture was stirred at 37° C. for a further 24 hours. The mixture was cooled to 0° C. and acidified to pH4 by the addition of glacial acetic acid. The precipitate was isolated and dried under vacuum. The precipitate was purified by column chromatography using a 9:1 mixture of methylene chloride and methanol as eluent. There was thus obtained the required starting material (0.7 g);

NMR Spectrum: (CD₃SOCD₃) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (s, 1H), 7.85 (d, 2H), 12.1 (broad s, 2H).

The methyl 2-amino-4-(tetrazol-5-yl)butyrate (in which the ratio of (S):(R) form was 7:3) used as a starting material was obtained as follows:

Sulphuryl chloride (1 g) was added to a stirred mixture of N-benzyloxycarbonyl-L-glutamine (100 g) and methanol (1200 ml) and the mixture was stirred at ambient temperature for 24 hours. The mixture was evaporated to give N-benzyloxycarbonyl-L-glutamine methyl ester (105 g).

p-Tosyl chloride (85.8 g) was added portionwise to a stirred mixture of the product so obtained and pyridine (200 ml) at such a rate that the temperature of the reaction mixture did not exceed 35° C. The mixture was then heated to 65° C. for 90 minutes. The mixture was concentrated by the evaporation of the pyridine and the residue was partitioned between ethyl acetate and water. The organic phase was washed with 2N aqueous hydrochloric acid and with water, dried (MgSO$_4$) and evaporated. The residue was purified by column chromatography using a 1:1 mixture of hexane and ethyl acetate as eluent. There was thus obtained methyl 2-benzyloxycarbonylamino-4-cyanobutyrate (81 g).

A mixture of the product so obtained, sodium azide (22.2 g), ammonium chloride (18.3 g) and DMF (400 ml) was heated on a steam bath for 24 hours. The mixture was concentrated and water (55 ml) was added to the residue. The mixture was acidified to pH1 by the addition of concentrated hydrochloric acid and extracted with ethyl acetate. The organic extract was dried (MgSO$_4$) and evaporated. The residue was triturated under diethyl ether to give methyl 2-benzyloxycarbonylamino-4-(tetrazol-5-yl)butyrate (36 g).

NMR Spectrum: (CD$_3$SOCD$_3$) 1.95–2.35 (m, 2H), 2.95 (t, 2H), 3.64 (s, 3H), 4.15 (m, 1H), 5.04 (s, 2H), 7.36 (s, 5H), 7.88 (d, 1H), 13.0 (s, 1H).

A mixture of a portion (17.1 g) of the product so obtained, 10% palladium-on-carbon catalyst (2.2 g) and ethanol (300 ml) was stirred at ambient temperature under an atmosphere of hydrogen for 24 hours. The mixture was filtered and the filtrate was evaporated. The residue was triturated under diethyl ether. There was thus obtained methyl 2-amino-4-(tetrazol-5-yl)butyrate (11.75 g), m.p. 177°–182° C.

EXAMPLE 4

Using an analogous procedure to that described in Example 3, p-[N-((6RS)-2-methyl-4-oxo-3,4,7,8-tetrahydro-6H-cyclopenta[g]quinazolin-6-yl)-N-(prop-2-ynyl)amino]benzoic acid was reacted with pentafluorophenol to give the pentafluorophenyl benzoate which was in turn reacted with dimethyl (2S)-2-aminoadipate to give dimethyl (2S)-2-{p-[N-((6RS)-2-methyl-4-oxo-3,4,7,8-tetrahydro-6H-cyclopenta[g]quinazolin-6-yl)-N-(prop-2-ynyl)amino]benzamido}adipate in 63% yield as a gum, which was in turn hydrolysed with aqueous sodium hydroxide solution to give
(2S)-2-{p-N-((6RS)-2-methyl-4-oxo-3,4,7,8-tetrahydro-6H-cyclopenta[g]quinazolin-6-yl)-N-(prop-2-ynyl)amino] benzamido}adipic acid in 79% yield, m.p. 176° C.;

NMR Spectrum: (CD$_3$SOCD$_3$): 1.6 (m, 2H), 1.8 (m, 2H), 2.25 (m, 3H), 2.35 (s, 3H), 2.5 (m, 1H), 3.0 (m, 2H), 3.1 (s, 1H), 3.85 (m, 1H), 4.1 (m, 1H), 4.35 (m, 1H), 5.75 (t, 1H), 7.0 (d, 2H), 7.5 (s, 1H), 7.85 (d, 2H), 7.85 (s, 1H), 8.25 (d, 1H), 12.0 (s, 2H);

Elemental Analysis: Found C, 56.2; H, 5.3; N, 9.2; C$_{28}$H$_{28}$N$_4$O$_6$ 2H$_2$O 0.75 NaCl requires C, 56.3; H, 5.4; N, 9.4%.

The p-[N-((6RS)-2-methyl-4-oxo-3,4,7,8-tetrahydro-6H-cyclopenta[g]quinazolin-6-yl)-N-(prop-2-ynyl)amino] benzoic acid used as a starting material was obtained as follows:

A mixture of N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid (6 g), carboxypeptidase G$_2$ (2000 units) tris buffer (750 ml) was stirred and heated to 37° C. for 30 hours. A second portion of carboxypeptidase G$_2$ (2000 units) was added and the mixture was heated to 37° C. for a further 24 hours. The mixture was cooled to 0° C. and acidified to pH4 by the addition of glacial acetic acid. The precipitate was isolated, washed with water and dried under vacuum. There was thus obtained the required starting material as a solid (4 g), m.p. 264° C.;

NMR Spectrum: (CD$_3$SOCD$_3$) 2.2 (m, 2H), 2.35 (s, 3H), 3.0 (m, 2H), 3.1 (s, 1H), 3.85 (m, 1H), 4.1 (m, 1H), 5.75 (t, 1H), 7.05 (d, 2H), 7.5 (s, 1H), 7.8 (s, 1H), 7.85 (d, 2H), 12.1 (broad s, 2H).

The dimethyl (2S)-2-aminoadipate was prepared by the reaction of (2S)-2-aminoadipic acid and methanol using an analogous procedure to that described (*J. Med. Chem.*, 1983, 26, 1719) for the preparation of the corresponding diethyl ester.

EXAMPLE 5

Using an analogous procedure to that described in Example 3, p-[N-((6RS)-2-methyl-4-oxo-3,4,7,8-tetrahydro-6H-cyclopenta[g]quinazolin- 6-yl)-N-(prop-2-ynyl)amino]benzoic acid was coupled to diethyl (2S)-2-aminopimelate (*J. Med. Chem.*, 1983, 26, 1719) and the resultant product was hydrolysed to give (2S)-2-{p-[N-((6RS)-2-methyl-4-oxo-3,4,7,8-tetrahydro-6H-cyclopenta[g] quinazolin-6-yl)-N-(prop-2-ynyl)amino]benzamido)pimelic acid in 25% yield, m.p. 165° C.;

NMR Spectrum: (CD$_3$SOCD$_3$) 1.4 (m, 2H), 1.55 (m, 2H), 1.8 (m, 2H), 2.2 (m, 3H), 2.35 (m, 3H), 2.5 (m, 1H), 3.0 (m, 2H), 3.1 (s, 1H), 3.85 (m, 1H), 4.1 (m, 1H), 4.35 (m, 1H), 5.75 (t, 1H), 7.0 (d, 2H), 7.5 (s, 1H), 7.8 (d, 2H), 7.85 (d, 1H), 8.2 (d, 1H), 12.0 (s, 2H).

EXAMPLE 6

Using an analogous procedure to that described in Example 1, dimethyl 2-}p-[N-(2-methyl-4-oxo-3-pivaloyloxymethyl-3,4,7,8-tetrahydro-6H-cyclopenta[g] quinazolin-6-yl)amino]benzamido]suberate was reacted with propargyl bromide and the resultant product was hydrolysed to give 2-{p-[N-(2-methyl-4-oxo-3,4,7,8-tetrahydro-6H-cyclopenta[g]quinazolin-6-yl)-N-(prop-2-ynyl)amino]benzamido}suberic acid, as a mixture of four isomers, in 28% yield, m.p.186° C.;

NMR Spectrum: (CD$_3$SOCD$_3$) 1.3 (m, 4H), 1.5 (m, 2H), 1.8 (m, 2H), 2.2 (t, 2H), 2.2 (m, 1H), 2.35 (s, 3H), 2.5 (m, 1H), 3.0 (m, 2H), 3.1 (s, 1H), 3.85 (m, 1H), 4.1 (m, 1H), 4.3 (m, 1H), 5.75 (t, 1H), 7.0 (d, 2H), 7.5 (s, 1H), 7.8 (d, 2H), 7.85 (s, 1H), 8.15 (d, 1H), 12.05 (s, 2H);

Elemental Analysis: Found C, 62.8; H, 6.2; N, 9.7; C$_{30}$H$_{32}$N$_4$O$_6$ 1.5 H$_2$O requires C, 63.0; H, 6.1; N, 9.8%.

The dimethyl 2-{p-[N-(2-methyl-4-oxo-3-pivaloyloxymethyl-3,4,7,8-tetrahydro-6H-cyclopenta[g] quinazolin-6-yl)amino]benzamido}suberate used as a starting material was obtained as follows:

A mixture of 6-bromo-2-methyl-3-pivaloyloxymethyl-3,4,7,8-tetrahydro-6H-cyclopenta[g]quinazolin-4-one (12.1 g), tert-butyl p-aminobenzoate (14.6 g), calcium carbonate (15.7 g) and DMA (200 ml) was stirred and heated to 115° C. for 45 minutes. The mixture was evaporated and the residue was partitioned between ethyl acetate and water. The organic phase was dried (MgSO$_4$) and evaporated. The residue was purified by column chromatography using increasingly polar mixtures of hexane and ethyl acetate as eluent. There was thus obtained tert-butyl p-[N-(2-methyl-4-oxo-3-pivaloyloxymethyl-3,4,7,8-tetrahydro-6H-cyclopenta[g]quinazolin-6-yl)amino]benzoate (4.1 g).

A mixture of a portion (3.6 g) of the material so obtained and trifluoroacetic acid (100 ml) was stirred at ambient temperature for 1 hour. The mixture was evaporated and the residue was triturated under diethyl ether (200 ml) to give p-[N-(2-methyl-4-oxo-3-pivaloyloxymethyl-3,4,7,8-tetrahydro-6H-cyclopenta[g]quinazolin-6-yl)amino]benzoic acid as a trifluoroacetic acid salt (3.2 g).

A mixture of the material so obtained, pentafluorophenol (2.6 g), N,N-dicyclohexylcarbodiimide (2.9 g) and methylene chloride (200 ml) was stirred at ambient temperature for 16 hours. The mixture was filtered and the filtrate was purified by column chromatography using increasingly polar mixtures of hexane and ethyl acetate as eluent. There was thus obtained pentafluorophenyl p-|N-(2-methyl-4-oxo-3-pivaloyloxymethyl-3,4,7,8-tetrahydro-6H-cyclopenta|g| quinazolin-6-yl)amino|benzoate as a gum (3 g).

A mixture of a portion (0.52 g) of the material so obtained, dimethyl 2-aminosuberate hydrochloride (*J. Med. Chem.*, 1983, 26, 1719; 0.288 g), triethylamine (1.25 ml), N-hydroxybenzotriazole (0.01 g) and DMF (20 ml) was stirred at ambient temperature for 16 hours. The mixture was evaporated and the residue was partitioned between ethyl acetate and water. The organic phase was dried (MgSO₄) and evaporated. The residue was purified by column chromatography using increasingly polar mixtures of hexane and ethyl acetate as eluent. There was thus obtained dimethyl 2-{p-|N-(2-methyl-4-oxo-3-pivaloyloxymethyl-3,4,7,8-tetrahydro-6H-cyclopenta[g]quinazolin-6-yl)amino| benzamido|suberate as a gum (0.36 g).

EXAMPLE 7

Using an analogous procedure to that described in the first paragraph of Example 3, p-|N-((6RS)-2-methyl-4-oxo-3,4,7,8-tetrahydro-6H-cyclopenta|g|quinazolin-6-yl)-N-(prop-2-ynyl)amino|benzoic acid was coupled to (2S)-2-amino-5-|(N-methylsulphonyl)carbamoyl|pentanoic acid to give (2S)-2-{p-|N-((6RS)-2-methyl-4-oxo-3,4,7,8-tetrahydro-6H-cyclopenta|g|quinazolin-6-yl)-N-(prop-2-ynyl)amino| benzamido}-5-[(N-methylsulphonyl)carbamoyl]pentanoic acid in 45% yield, m.p. 173° C.;

NMR Spectrum: (CD₃SOCD₃) 1.65 (m, 2H), 1.8 (m, 2H), 2.3 (t, 2H), 2.3 (m, 1H), 2.35 (s, 3H), 2.5 (m, 1H), 3.05 (m, 2H), 3.1 (s, 1H), 3.2 (s, 3H), 3.85 (m, 1H), 4.1 (m, 1H), 4.35 (m, 1H), 5.75 (t, 1H), 7.0 (d, 2H), 7.5 (s, 1H), 7.8 (s, 1H), 7.8 (d, 2H), 8.25 (d, 1H), 11.65 (s, 1H), 12.1 (s, 1H), 12.45 (s, 1H);

Elemental Analysis: Found C, 55.9; H, 5.4; N, 11.1; $C_{29}H_{31}N_5O_7S$ 1.75 $H_2O$ requires C, 55.7; H, 5.5; N, 11.2%.

The (2S)-2-amino-5-|(N-methylsulphonyl)carbamoyl| pentanoic acid used as a starting material was obtained as follows:

Benzyl chloroformate (15.5 g) was added dropwise to a stirred mixture of (2S)-2-aminoadipic acid (12 g) and sodium carbonate (39.4 g) which had been cooled to 5° C. The mixture was stirred at ambient temperature for 16 hours. The mixture was washed with diethyl ether. The aqueous phase was acidified to pH1 by the addition of dilute aqueous hydrochloric acid and extracted with ethyl acetate. The organic phase was dried (MgSO₄) and evaporated to give (2S)-2-benzyloxycarbonylaminoadipic acid (21.6 g).

Triethylamine (15.8 ml) and benzyl chloride (12.7 ml) were added in turn to a stirred mixture of (2S)-2-benzyloxycarbonylaminoadipic acid (21.6 g) and DMF (200 ml). The mixture was stirred at ambient temperature for 16 hours. Triethylamine (8 ml), benzyl chloride (6.35 ml) and 4-dimethylaminopyridine (0.1 g) were added in turn and the mixture was stirred at ambient temperature for 24 hours. The mixture was evaporated and the residue was partitioned between ethyl acetate and dilute aqueous hydrochloric acid. The organic layer was dried (MgSO₄) and evaporated. The residue was purified by column chromatography using increasingly polar mixtures of hexane and ethyl acetate as eluent. There was thus obtained 1-benzyl (2S)-2-benzyloxy carbonylaminoadipate (12.5 g).

N,N-Dicyclohexylcarbodiimide (4.2 g) was added to a mixture of a portion (4 g) of the adipate so obtained, methanesulphonamide (1.93 g), 4-dimethylaminopyridine (2.5 g) and methylene chloride (120 ml). The mixture was stirred at ambient temperature for 16 hours. The mixture was evaporated and the residue was partitioned between ethyl acetate and dilute aqueous hydrochloric acid. The organic phase was dried (MgSO₄) and evaporated. The residue was purified by column chromatography using increasingly polar mixtures of hexane and ethyl acetate as eluent. There was thus obtained 1-benzyl (2S,)-2-benzyloxycarbonylamino-5-|(N-methylsulphonyl)carbamoyl|-pentanoate (6.3 g).

A mixture of the material so obtained, 10% palladium-on-carbon catalyst (1 g) and acetic acid (100 ml) was stirred under an atmosphere of hydrogen for 16 hours. The mixture was filtered and the filtrate was evaporated to give (2S)-2-amino-5-|(N-methylsulphonyl)carbamoyl|pentanoic acid (2.46 g).

EXAMPLE 8

Using an analogous procedure to that described in the first paragraph of Example 3, p-|N-((6RS)-2-methyl-4-oxo-3,4,7,8-tetrahydro-6H-cyclopenta[g]quinazolin-6-yl)-N-(prop-2-ynyl)amino| benzoic acid was coupled to (2R)-2-amino-3-(tetrazol-5-ylthio)propionic acid to give (2R)-2-{p-[N-((6RS)-2-methyl-4-oxo-3,4,7,8-tetrahydro-6H-cyclopenta|g|quinazolin-6-yl)-N-(prop-2-ynyl) amino]benzamido}-3-(tetrazol-5-ylthio)propionic acid in 48% yield, m.p. 178° C.;

NMR Spectrum: 2.2 (m, 1H), 2.35 (s, 3H), 2.5 (m, 1H), 3.05 (m, 2H), 3.1 (s, 1H), 3.55 (d, 1H), 3.65 (d, 1H), 3.8 (m, 1H), 4.1 (m, 1H), 4.7 (m, 1H), 5.75 (t, 1H), 7.05 (d, 2H), 7.5 (s, 1H), 7.75 (d, 2H), 7.8 (s, 1H), 8.6 (d, 1H), 12.2 (s, 1H);

Elemental Analysis: Found C, 55.2; H, 5.0; N, 18.8; $C_{26}H_{24}N_8O_4S$ 1.5$H_2O$ requires C, 54.6; H, 4.7; N, 19.6%.

The (2R)-2-amino-3-(tetrazol-5-ylthio)propionic used as a starting material was obtained as follows:

A mixture of (2R)-3-chloroalanine hydrochloride (18.5 g), tetrazole-5-thiol (11.79 g) and 2N aqueous sodium hydroxide solution (230 ml) was stirred and heated to 90° C. for 2.5 hours. The mixture was cooled in an ice-bath and acidified to pH4 by the addition of concentrated hydrochloric acid. The precipitate was isolated, washed with water and dried. There was thus obtained (2R)-2-amino-3-(tetrazol-5-ylthio)propionic acid (8 g).

The tetrazole-5-thiol was obtained as follows:

Sodium (20 g) was added portionwise to a mixture of benzyl tetrazol-5-yl sulphide (European Patent Application No. 33965; 50 g) and pyridine (400 ml) which had been warmed to 60° C. The mixture was heated to reflux for 2 hours. The mixture was allowed to cool to 45° C. and methanol (75 ml) was added. The mixture was evaporated and the residue was partitioned between ethyl acetate and water. The aqueous phase was acidified to pH2 by the addition of concentrated hydrochloric acid and extracted with ethyl acetate. The organic extract was dried (MgSO₄) and evaporated to give tetrazole-5-thiol (15.4 g).

EXAMPLE 9

Using an analogous procedure to that described in the first paragraph of Example 1, N-(3-cyanobenzyl)-p-|N-((6RS)-2-methyl-4-oxo-3-pivaloyloxymethyl-3,4,7,8-tetrahydro-6H-cyclopenta|g|quinazolin-6-yl)amino|benzamide (0.36 g) was reacted with propargyl bromide to give N-(3-cyanobenzyl)-p-|N-(2-methyl-4-oxo-3-pivaloyloxymethyl-3,4,7,8-tetrahydro-6H-cyclopenta|g|quinazolin-6-yl)-N-(prop-2-ynyl)amino|benzamide (0.154 g).

A mixture of a portion (0.144 g) of the material so obtained and a saturated solution of ammonia gas in methanol (30 ml) was stirred at ambient temperature for 16 hours. The mixture was evaporated. The residue was triturated under diethyl ether (5 ml) to give N-(3-cyanobenzyl)-p-[N-((6RS)-2-methyl-4-oxo-3,4,7,8-tetrahydro-6H-cyclopenta [g]quinazolin-6-yl)-N-(prop-2-ynyl)amino]benzamide (0.105 g), m.p. 260° C.;

NMR Spectrum: $(CD_3SOCD_3)$ 2.2 (m, 1H), 2.35 (s, 3H), 2.5 (m, 1H), 3.0 (t, 1H), 3.1 (m, 2H), 3.85 (m, 1H), 4.1 (m, 1H), 4.5 (d, 2H), 5.75 (t, 1H), 7.0 (d, 2H), 7.5 (s, 1H), 7.55 (d, 1H), 7.65 (m, 2H), 7.75 (s, 1H), 7.8 (s, 1H), 7.85 (d, 2H), 8.8 (t, 1H).

Elemental Analysis: Found C, 71.9; H, 5.1; N, 14.1; $C_{30}H_{25}N_5O_2$ 0.75$H_2O$ requires C, 71.9; H, 5.3; N, 14.0%.

The N-(3-cyanobenzyl)-p-[N-((6RS)-2-methyl-4-oxo-3-pivaloyloxymethyl-3,4,7,8-tetrahydro-6H-cyclopenta[g] quinazolin-6-yl)amino]benzamide used as a starting material was obtained as follows:

A mixture of pentafluorophenyl p-[N-(6RS)-2-methyl-4-oxo-3-pivaloyloxymethyl-3,4,7,8-tetrahydro-6H-cyclopenta [g]quinazolin-6-yl)amino]benzoate (0.5 g), 3-cyanobenzylamine (*J. Med. Chem.*, 27, 111; 0.421 g), triethylamine (0.841 g), N-hydroxybenzotriazole (0.01 g) and DMA (20 ml) was stirred at ambient temperature for 16 hours. The mixture was evaporated and the residue was partitioned between ethyl acetate and water. The organic phase was dried ($MgSO_4$) and evaporated. The residue was purified by column chromatography using increasingly polar mixtures of hexane and ethyl acetate as eluent. There was thus obtained the required starting material (0.37 g).

EXAMPLE 10

A mixture of pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)amino]benzoate (0.7 g), diethyl L-glutamate (0.5 g), triethylamine (1.1 g), N-hydroxybenzotriazole (0.01 g) and DMA (30 ml) was stirred at ambient temperature for 16 hours. The mixture was evaporated and the residue was partitioned between ethyl acetate and water. The organic phase was dried ($MgSO_4$) and evaporated. The residue was purified by column chromatography using increasingly polar mixtures of hexane and ethyl acetate as eluent. There was thus obtained diethyl N-{o-fluoro-p-[N-((6RS)-2-methyl-4-oxo-3-pivaloyloxymethyl-3,4,7,8-tetrahydro-6H-cyclopenta[g]quinazolin-6-yl)amino]-benzoyl}-L-glutamate as a gum (0.64 g);

NMR Spectrum: $(CDCl_3)$ 1.2 (s, 9H), 1.25 (t, 3H), 1.3 (t, 3H), 2.05 (m, 2H), 2.32 (m, 1H), 2.45 (m, 2H), 2.65 (s, 3H), 2.72 (m, 1H), 3.05 (m, 1H), 3.2 (m, 1H), 4.12 (m, 2H), 4.25 (q, 2H), 4.35 (m, 1H), 4.5 (d, 1H), 5.09 (2 d's, 1H), 6.1 (2 d's, 2H), 6.4 (2 t's, 1H), 6.53 (2 t's, 1H), 7.2 (2 d's, 1H), 7.5 (s, 1H), 7.93 (t, 1H), 8.2 (s, 1H).

A mixture of a portion (0.1 g) of the material so obtained, 2N aqueous sodium hydroxide (0.5 ml) and methanol (5 ml) was stirred at ambient temperature for 24 hours. The mixture was concentrated by the evaporation of the bulk of the methanol. Water (20 ml) was added and the mixture was acidified to pH5 by the addition of 2N aqueous hydrochloric acid. The precipitate was isolated, washed with water and dried under vacuum. There was thus obtained N-{o-fluoro-p-[N-((6RS)-2-methyl-4-oxo-3,4,7,8-tetrahydro-6H-cyclopenta[g]quinazolin-6-yl)amino]benzoyl}-L-glutamic acid (0.06 g), m.p. 198°–201° C.;

NMR Spectrum: $(CD_3SOCD_3)$ 1.95 (m, 4H), 2.29 (m, 2H), 2.32 (s, 3H), 3.0 (m, 2H), 4.4 (2 d's, 1H), 5.15 (2 d's, 1H), 6.55 (2 d's, 1H), 6.65 (2 d's, 1H), 7.45 (s, 1H), 7.55 (t, 1H), 7.75 (t, 1H), 7.9 (s, 1H), 7.95 (d, 1H), 12.08 (broad s, 1H), 12.5 (broad s, 1H);

Elemental Analysis: Found C, 57.0; H, 4.7; N, 10.9; $C_{24}H_{23}FN_4O_6$ 1.25$H_2O$ requires C, 57.0; H, 5.0; N, 11.1%.

The pentafluorophenyl o-fluoro-p-[N-(6RS)-2-methyl-4-oxo-3-pivaloyloxymethyl-3,4,7,8-tetrahydro-6H-cyclopenta [g]quinazolin-6-yl)-amino]benzoate used as a starting material was obtained as follows:

A mixture of 6-bromo-2-methyl-3-pivaloyloxymethyl-3, 4,7,8-tetrahydro-6H-cyclopenta[g]quinazolin-4-one (26 g), p-amino-o-fluorobenzoic acid 1,1-dimethyl-2-hydroxyethylammonium salt (42 g), calcium carbonate (21.4 g) and DMSO (200 ml) was stirred at ambient temperature for 72 hours. The mixture was poured onto a mixture of ice and water (1 liter). The precipitate was isolated, washed with water and dried under vacuum. The product was purified by column chromatography using initially a 9:1 mixture of methylene chloride and methanol and then a 9:1:0.1 mixture of methylene chloride, methanol and acetic acid as eluent. There was thus obtained o-fluoro-p-[N-((6RS)-2-methyl-4-oxo-3-pivaloyloxymethyl-3,4,7,8-tetrahydro-6H-cyclopenta[g]quinazolin-6-yl)amino]benzoic acid as a gum (20 g).

A mixture of a portion (0.75 g) of the material so obtained, pentafluorophenol (1.77 g), N,N-dicyclohexylcarbodiimide (0.66 g), N-hydroxybenzotriazole (0.01 g) and methylene chloride (100 ml) was stirred at ambient temperature for 18 hours. The mixture was filtered and the filtrate was evaporated. The residue was purified by column chromatography using increasingly polar mixtures of hexane and ethyl acetate as eluent. There was thus obtained pentafluorophenyl o-fluoro-p-[N-((6RS)-2-methyl-4-oxo-3-pivaloyloxymethyl-3,4,7,8-tetrahydro-6H-cyclopenta[g] quinazolin-6-yl)amino]benzoate as a gum (0.72 g);

NMR Spectrum: $(CDCl_3)$ 1.23 (s, 9H), 2.05 (m, 1H), 2.65 (s, 3H), 2.75 (m, 1H), 3.13 (m, 2H), 4.8 (d, 1H), 5.15 (s d's, 1H), 6.1 (2 d's, 2H ), 6.3 (m, 2H), 7.5 (s, 1H), 7.95 (t, 1H), 8.2 (s, 1H).

EXAMPLE 11

An aqueous solution of formaldehyde (37% weight/volume, 0.45 ml) was added dropwise to a stirred solution of diethyl N-{o-fluoro-p-[N-((6RS)-2-methyl-4-oxo-3-pivaloyloxymethyl-3,4,7,8-tetrahydro-6H-cyclopenta[g] quinazolin-6-yl)amino]benzoyl}-L-glutamate (0.34 g) in glacial acetic acid (10 ml). The mixture was stirred at ambient temperature for 45 minutes. Sodium cyanoborohydride (0.07 g) was added portionwise during 5 minutes and the mixture was stirred at ambient temperature for 30 minutes. The mixture was poured onto a mixture of ice and water (50 ml) and extracted with ethyl acetate. The organic phase was dried ($MgSO_4$) and evaporated. The residue was purified by column chromatography using increasingly polar mixtures of hexane and ethyl acetate as eluent. There was thus obtained diethyl N-{o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzoyl}-L-glutamate as a gum (0.195 g);

NMR Spectrum: $(CDCl_3)$ 1.2 (s, 9H), 1.25 (t, 3H), 1.3 (t, 3H), 2.1 (m, 2H), 2.35 (m, 1H), 2.47 (m, 3H), 2.63 (s, 3H), 2.74 (s, 3H), 2.9 (m, 1H), 3.1 (m, 2H), 4.12 (q, 2H), 4.25 (q, 2H), 4.85 (m, 1H), 5.59 (t, 1H), 6.1 (2 d's, 2H), 6.52 (2 t's, 1H), 7.22 (2 d's, 1H), 7.52 (s, 1H), 7.96 (t, 1H), 8.03 (s, 1H).

A mixture of the material so obtained, 1N aqueous sodium hydroxide (2 ml) and methanol (10 ml) was stirred at ambient temperature for 24 hours. The bulk of the methanol was evaporated and the residue was dissolved in water (20 ml). The solution was acidified to pH5 by the addition of 2N aqueous hydrochloric acid. The precipitate was isolated, washed with water and dried under vacuum. There was thus obtained N-{o-fluoro-p-|N-methyl-N-((6RS)-2-methyl-4-oxo-3,4,7,8-tetrahydro-6H-cyclopenta[g]quinazolin-6-yl)amino|benzoyl}-L-glutamic acid (0.12 g), m.p. 228° C.;

NMR Spectrum: (CD$_3$SOCD$_3$) 2.05 (m, 4H), 2.3 (s, 3H), 2.4 (m, 2H), 2.65 (s, 3H), 3.0 (m, 2H), 4.45 (2 d's, 1H), 5.7 (t, 1H), 6.68 (2 d's, 1H), 6.82 (2 d's, 1H), 7.45 (s, 1H), 7.64 (d, 1H), 7.7 (s, 1H), 7.85 (t, 1H), 12.1 (broad s, 1H);

Elemental Analysis: Found C, 55.6; H, 5.0; N, 10.3; $C_{25}H_{25}FN_4O_6$ 1.5H$_2$O 0.25NaCl requires C, 55.7; H, 5.2; N, 10.4%.

EXAMPLE 12

A mixture of 5-|N-methyl-N-((6RS)-2-methyl-4-oxo-3,4,7,8-tetrahydro-6H-cyclopenta[g]quinazolin-6-yl)amino| pyridine-2-carboxylic acid (0.01 g), pentafluorophenyl trifluoroacetate (0.16 g; prepared by the reaction of pentafluorophenol and trifluoroacetic acid), pyridine (0.045 g) and DMA (5 ml) was stirred at ambient temperature for 5 hours. The mixture was evaporated and the residue was partitioned between ethyl acetate and a saturated aqueous sodium bicarbonate solution. The organic phase was dried (MgSO$_4$) and evaporated. The residue was purified by column chromatography using increasingly polar mixtures of ethyl acetate and methanol as eluent. There was thus obtained pentafluorophenyl 5-[N-methyl-N-((6RS)-2-methyl-4-oxo-3,4,7,8-tetrahydro-6H-cyclopenta[g] quinazolin-6-yl)amino]pyridine-2-carboxylate as a foam (0.1 g);

NMR Spectrum: (CD$_3$SOCD$_3$) 2.1 (m, 1H), 2.35 (s, 3H), 2.55 (m, 1H), 2.81 (s, 3H), 3.1 (m, 2H), 5.98 (t, 1H), 7.48 (2 d's, 1H), 7.5 (s, 1H), 7.75 (s, 1H), 8.14 (d, 1H), 8.57 (d, 1H), 12.19 (s, 1H).

A mixture of the material so obtained, methyl (2S)-2-amino-4-(tetrazol-5-yl)butyrate (0.054 g), triethylamine (0.28 ml), N-hydroxybenzotriazole (0.01 g) and DMA (10 ml) was stirred at ambient temperature for 24 hours. The mixture was evaporated and the residue was partitioned between ethyl acetate and water. The organic phase was washed with water, dried (MgSO$_4$) and evaporated. The residue was purified by column chromatography using initially ethyl acetate and then a 9:1 mixture of methylene chloride and methanol as eluent. There was thus obtained methyl (2S)-2-{5-[N-methyl-N-((6RS)-2-methyl-4-oxo-3,4,7,8-tetrahydro-6H-cyclopenta[g]quinazolin-6-yl)amino] pyridine-2-carboxamido}-4-(tetrazol-5-yl)butyrate as a gum (0.1 g).

A mixture of the material so obtained, 1N aqueous sodium hydroxide (1 ml) and methanol (10 ml) was stirred at ambient temperature for 24 hours. The mixture was concentrated by the evaporation of the bulk of the methanol. Water (10 ml) was added and the mixture was acidified to pH4.5 by the addition of 2N aqueous hydrochloric acid. The precipitate was isolated, washed with water and dried under vacuum. There was thus obtained (2S)-2-{5-[N-methyl-N-((6RS)-2-methyl-4-oxo-3,4,7,8-tetrahydro-6H-cyclopenta[g] quinazolin-6-yl)amino|pyridine-2-carboxamido-4-(tetrazol-5-yl)butyric acid (0.052 g), m.p. 248°–250° C.;

NMR Spectrum: (CD$_3$SOCD$_3$) 2.15 (m, 3H), 2.35 (s, 3H), 2.75 (s, 3H), 3.0 (m, 5H), 4.48 (2 d's, 1H), 5.85 (t, 1H), 7.45 (2 t's, 1H), 7.5 (s, 1H), 7.73 (s, 1H), 7.88 (d, 1H), 8.35 (s, 1H), 8.6 (d, 1H), 12.12 (broad s, 1H);

Elemental Analysis: Found C, 51.7; H, 5.3; N, 22.6; $C_{24}H_{25}N_9O_4$ 3H$_2$O requires C, 51.7; H, 5.5; N, 22.6%.

The 5-|N-methyl-N-((6RS)-2-methyl-4-oxo-3,4,7,8-tetrahydro-6H-cyclopenta[g]quinazolin-6-yl)amino| pyridine-2-carboxylic acid used as a starting material was obtained as follows:

A solution of methyl 5-|N-(tert-butoxycarbonyl)amino|-pyridine-2-carboxylate (*J. Med. Chem.*, 1991, 1594; 0.32 g) in DMA (10 ml) was added dropwise to a stirred suspension of sodium hydride |60% dispersion in mineral oil, 0.051 g, from which the oil was removed using hexane| in DMA (5 ml). The mixture was stirred at ambient temperature for 30 minutes. This mixture was added dropwise to a stirred solution of 6-bromo-2-methyl-3-pivaloyloxymethyl-3,4,7,8-tetrahydro-6H-cyclopenta[g]quinazolin-4-one (0.5 g) in DMA (10 ml) which had been cooled to −10° C. The resultant mixture was stirred at ambient temperature for 18 hours. The mixture was evaporated and the residue was partitioned between ethyl acetate and water. The organic phase was dried (MgSO$_4$) and evaporated. The residue was purified by column chromatography using increasingly polar mixtures of hexane and ethyl acetate to give methyl 5-[N-(tert-butoxycarbonyl)-N-((6RS)-2-methyl-4-oxo-3-pivaloyloxymethyl-3,4,7,8-tetrahydro-6H-cyclopenta[g] quinazolin-6-yl)amino]pyridine-2-carboxylate as a gum (0.3 g).

A mixture of the gum so obtained and trifluoroacetic acid (10 ml) was stirred at ambient temperature for 1 hour. The mixture was evaporated and the residue was partitioned between ethyl acetate and a saturated aqueous sodium bicarbonate solution. The organic phase was dried (MgSO$_4$) and evaporated. The residue was purified by column chromatography using increasingly polar mixtures of hexane and ethyl acetate as eluent. There was thus obtained methyl 5-[N-((6RS)-2-methyl-4-oxo-3-pivaloyloxymethyl-3,4,7,8-tetrahydro-6H-cyclopenta[g]quinazolin-6-yl)amino| pyridine-2-carboxylate (0.24 g);

NMR Spectrum: (CDCl$_3$) 1.2 (s, 9H), 2.02 (m, 1H), 2.52 (m, 1H), 2.64 (s, 3H), 3.12 (m, 2H), 3.98 (s, 3H), 4.56 (d, 1H), 5.15 (2 d's, 1H), 6.1 (2 d's, 2H), 7.02 (2 d's, 1H), 7.5 (s, 1H), 8.0 (d, 1H), 8.18 (d, 1H), 8.22 (s, 1H).

A mixture of the product so obtained, an aqueous solution of formaldehyde (37% weight/volume, 0.52 ml) and glacial acetic acid (5 ml) was stirred at ambient temperature for 30 minutes. Sodium cyanoborohydride (0.05 g) was added portionwise during 5 minutes and the mixture was stirred at ambient temperature for 30 minutes. The mixture was poured onto a mixture of ice and water (20 ml) and extracted with ethyl acetate. The organic phase was dried (MgSO$_4$) and evaporated. The residue was purified by column chromatography using ethyl acetate as eluent. There was thus obtained methyl 5-[N-methyl-N-((6RS)-2-methyl-4-oxo-3-pivaloyloxymethyl-3,4,7,8-tetrahydro-6H-cyclopenta[g] quinazolin-6-yl)amino|pyridine-2-carboxylate as a gum (0.185 g);

NMR Spectrum: (CDCl$_3$) 1.22 (s, 9H), 2.15 (m, 1H), 2.57 (m, 1H), 2.64 (s, 3H), 2.82 (s, 3H), 3.13 (m, 2H), 3.98 (s, 3H), 5.65 (t, 1H), 6.1 (2 d's, 2H), 7.15 (2 d's, 1H), 7.52 (s, 1H), 8.03 (d, 1H), 8.06 (s, 1H), 8.35 (d, 1H).

A mixture of the product so obtained, sodium hydroxide (0.06 g), water (2 ml) and methanol (10 ml) was stirred at ambient temperature for 18 hours. The mixture was evaporated. Water (20 ml) was added and the mixture was acidified to pH5 by the addition of 2N aqueous hydrochloric acid. The precipitate was isolated, washed with water and dried under vacuum. There was thus obtained 5-|N-methyl-N-( (6RS)-2-methyl-4-oxo-3,4,7,8-tetrahydro-6H-cyclopenta[g]
quinazolin-6-yl)amino]pyridine-2-carboxylic acid (0.01 g).

The methyl (2S)-2-amino-4-(tetrazol-5-yl)butyrate (in which the ratio of (S):(R) form was 99:1 or greater) used as a starting material was obtained as follows:

A solution of N-benzyloxycarbonyl-L-glutamine methyl ester (25 g) in THF (500 ml) was added dropwise to a stirred solution of triphenylphosphine (44.5 g) in carbon tetrachloride (1 L). The mixture was heated to 50° C. for 2 hours. The mixture was evaporated. The resultant oil was triturated in ethyl acetate. The mixture was filtered and the filtrate was evaporated. The residue was purified by column chromatography using a 1:1 mixture of hexane and ethyl acetate as eluent. There was thus obtained methyl (2S)-2-benzyloxycarbonylamino-4-cyanobutyrate (19.38 g, 83%).

A mixture of methyl (2S)-2-benzyloxycarbonylamino-4-cyano-butyrate (10 g), tri-n-butyltin azide [prepared according to the method in Rec. Trav. Chim. Pays-Bas, 1963, 81, 286; 12 g] and THF (60 ml) was stirred and heated to reflux for 40 hours. The mixture was evaporated. The resultant brown oil was triturated in diethyl ether which had been saturated with hydrogen chloride gas. The precipitate was isolated and washed with diethyl ether. There was thus obtained methyl (2S)-2-benzyloxycarbonylamino-4-(tetrazol-5-yl)butyrate (2.23 g, 32%).

NMR Spectrum: (CD$_3$SOCD$_3$) 1.95–2.35 (m, 2H), 2.95 (t, 2H), 3.64 (s, 3H), 4.15 (m, 1H), 5.04 (s, 2H), 7.36 (s, 5H), 7.88 (d, 1H), 13.0 (s, 1H).

A mixture of the product so obtained, 10% palladium-on-carbon catalyst (0.3 g) and ethanol (30 ml) was stirred at ambient temperature under an atmosphere of hydrogen for 24 hours. The mixture was filtered and the filtrate was evaporated. The residue was triturated under diethyl ether. There was thus obtained methyl (2S)-2-amino-4-(tetrazol-5-yl)butyrate in 88% yield.

NMR Spectrum: (CD$_3$SOCD$_3$) 1.82–2.26 (m, 2H), 2.86–2.94 (t, 2H), 3.67 (s, 3H), 3.7–3.85 (m, 1H), 5.28 (broad s, 2H).

EXAMPLE 13

Using analogous procedures to those described in Example 12, 5-[N-((6RS)-2-methyl-4-oxo-3,4,7,8-tetrahydro-6H-cyclopenta[g]quinazolin-6-yl)-N-(prop-2-ynyl)amino]pyridine-2-carboxylic acid was reacted with methyl (2S)-2-amino-4-(tetrazol-5-yl)butyrate to give (2S)-2-{5-[N-((6RS)-2-methyl-4-oxo-3,4,7,8-tetrahydro-6H-cyclopenta[g]quinazolin-6-yl)-N-(prop-2-ynyl)amino]pyridine-2-carboxamido}-4-(tetrazol-5-yl)butyric acid in 33% yield, m.p. 189°–191° C.;

NMR Spectrum: (CD$_3$SOCD$_3$) 2.3 (m, 5H), 2.35 (s, 3H), 2.95 (m, 3H), 3.0 (s, 1H), 3.9 (2 d's, 1H), 4.15 (2 d's, 1H), 4.52 (2 d's, 1H), 5.75 (t, 1H), 7.42 (2 t's, 1H), 7.5 (s, 1H), 7.84 (s, 1H), 7.9 (d, 1H), 8.18 (t, 1H), 8.55 (d, 1H), 12.1 (broad s, 1H);

Elemental Analysis: Found C, 55.9; H, 4.9; N, 21.8; C$_{26}$H$_{25}$N$_9$O$_4$ 2.5H$_2$O requires C, 55.4; H, 5.3; N, 22.3%.

The 5-[N-((6RS)-2-methyl-4-oxo-3,4,7,8-tetrahydro-6H-cyclopenta[g]quinazolin-6-yl)-N-(prop-2-ynyl)amino] pyridine-2-carboxylic acid used as a starting material was obtained as follows:

A solution of potassium tert-butoxide (8.6 g) in a mixture of tert-butanol (100 ml) and DMA (100 ml) was added dropwise during 20 minutes to a stirred solution of a mixture of 6-bromo-2-methyl-3-pivaloyloxymethyl-3,4,7,8-tetrahydro-6H-cyclopenta[g]quinazolin-4-one (30 g) and methyl 5-[N-(prop-2-ynyl)amino]pyridine-2-carboxylate [14.5 g; obtained in quantitative yield by treating methyl 5-[N-(tert-butoxycarbonyl)-N-(prop-2-ynyl)amino] pyridine-2-carboxylate (J. Med. Chem., 1991, 1594) with trifluoroacetic acid at 0° C. for 1 hour] in DMA (300 ml) which had been cooled to −20° C. The mixture was allowed to warm to ambient temperature and was stirred for 24 hours. The mixture was evaporated. A mixture of ice and water (1 L) was added to the residue and the mixture was extracted with ethyl acetate. The organic phase was dried (MgSO$_4$) and evaporated. The residue was purified by column chromatography using initially increasingly polar mixtures of hexane and ethyl acetate and then a 19:1 mixture of methylene chloride and methanol as eluent. There was thus obtained methyl 5-[N-((6RS)-2-methyl-4-oxo-3-pivaloyloxymethyl-3,4,7,8-tetrahydro-6H-cyclopenta[g] quinazolin-6-yl)-N-(prop-2-ynyl)amino]pyridine-2-carboxylate (10.1 g);

NMR Spectrum: (CDCl$_3$) 1.2 (s, 9H), 2.25 (t, 1H), 2.35 (m, 1H), 2.6 (m, 1H), 2.65 (s, 3H), 3.1 (m, 1H), 3.3 (m, 1H), 3.88 (2 d's, 1H), 3.98 (s, 3H), 4.03 (2 d's, 1H), 5.65 (t, 1H), 6.1 (2 d's, 2H), 7.3 (2 d's, 1H), 7.55 (s, 1H), 8.08 (d, 1H), 8.1 (s, 1H), 8.4 (s, 1H).

A mixture of a portion (1 g) of the product so obtained, sodium hydroxide (0.32 g), water (10 ml) and methanol (30 ml) was stirred at ambient temperature for 24 hours. The mixture was evaporated. Water (60 ml) was added and the mixture was acidified to pH5 by the addition of 2N aqueous hydrochloric acid. The precipitate was isolated, washed with water and dried under vacuum. There was thus obtained 5-[N-((6RS)-2-methyl-4-oxo-3,4,7,8-tetrahydro-6H-cyclopenta[g]quinazolin-6-yl)-N-(prop-2-ynyl)amino] pyridine-2-carboxylic acid (0.68 g);

NMR Spectrum: (CD$_3$SOCD$_3$) 2.25 (m, 1H), 2.3 (s, 3H), 2.5 (m, 1H), 3.0 (s, 1H), 3.05 (m, 2H), 3.9 (2 d's, 1H), 4.15 (2 d's, 1H), 5.8 (t 1H) 7.4 (2 d's, 1H)$_7$ 7.5 (s, 1H), 7.8 (s, 1H), 7.9 (d, 1H), 8.35 (d, 1H)

EXAMPLE 14

Using analogous procedures to those described in Example 12, 5-[N-((6RS)-2-methyl-4-oxo-3,4,7,8-tetrahydro-6H-cyclopenta[g]quinazolin-6-yl)-N-(prop-2-ynyl)amino]pyridine-2-carboxylic acid was reacted with pentafluorophenyl trifluoroacetate to give the pentafluorophenyl pyridine-2-carboxylate which was in turn reacted with diethyl L-glutamate to give diethyl N-{5-[N-((6RS)-2-methyl-4-oxo-3,4,7,8-tetrahydro-6H-cyclopenta[g] quinazolin-6-yl)-N-(prop-2-ynyl)amino|pyridyl-2-carbonyl}-L-glutamate in 93% yield which was in turn hydrolysed with aqueous sodium hydroxide solution to give N-{5-[N-((6RS)-2-methyl-4-oxo-3,4,7,8-tetrahydro-6H-cyclopenta[g]quinazolin-6-yl)-N-(prop-2-ynyl)amino] pyridyl-2-carbonyl}-L-glutamic acid in 77% yield, m.p. 199°–201° C.;

NMR Spectrum: (CD$_3$SOCD$_3$) 2.15 (m, 5H), 2.35 (s, 3H), 3.05 (m, 3H), 3.2 (s, 1H), 3.95 (2 d's, 1H), 4.2 (2 d's, 1H), 4.48 (m, 1H), 5.8 (t, 1H), 7.49 (2 t's, 1H), 7.5 (s, 1H), 7.85 (s, 1H), 7.89 (d, 1H), 8.3) (d, 1H), 8.48 (d, 1H), 12.1 (broad s, 1H), 12.5 (broad s, 1H);

Elemental Analysis: Found C, 60.3; H, 5.1; N, 13.4; C$_{26}$H$_{25}$N$_5$O$_6$ 1H$_2$O requires C, 59.8; H, 5.2; N, 13.4%.

EXAMPLE 15

Using analogous procedures to those described in Example 12, 5-|N-((6RS)-2-methyl-4-oxo-3,4,7,8-tetrahydro-6H-cyclopenta[g]quinazolin-6-yl)-N-(prop-2-ynyl)amino|pyridine-2-carboxylic acid was reacted with pentafluorophenyl trifluoroacetate to give the pentafluorophenyl pyridine-2-carboxylate which was in turn reacted with tri-tert-butyl L-γ-glutamyl-D-glutamate (European Patent Application No. 0509643, Example 1 thereof) to give tri-tert-butyl N-{5-[N-((6RS)-2-methyl-4-oxo-3,4,7,8-tetrahydro-6H-cyclopenta[g]quinazolin-6-yl)-N-(prop-2-ynyl)amino|pyridyl-2-carbonyl -L-γ-glutamyl-D-glutamate in 98% yield which was in turn hydrolysed with aqueous sodium hydroxide solution to give N-{5-[N-((6RS)-2-methyl-4-oxo-3,4,7,8-tetrahydro-6H-cyclopenta[g]quinazolin-6-yl)-N-(prop-2-ynyl)amino|pyridyl-2-carbonyl}-L-γ-glutamyl-D-glutamic acid in 68% yield, m.p. 196° C.;

NMR Spectrum: (CD$_3$SOCD$_3$) 2.0 (m, 4H), 2.2 (m, 5H), 2.35 (s, 3H), 2.5 (m, 1H), 3.0 (m, 1H), 3.2 (s, 1H), 3.3 (m, 1H), 3.95 (d, 1H), 4.2 (d, 1H), 4.22 (m, 1H), 4.45 (m, 1H), 5.8 (t, 1H), 7.45 (2 t's, 1H), 7.5 (s, 1H), 7.85 (s, 1H), 7.9 (d, 1H), 8.1 (d, 1H), 8.35 (t, 1H), 8.45 (d, 1H), 12.1 (s, 1H), 12.5 (broad s, 1H);

Elemental Analysis: Found C, 53.8; H, 5.2; N, 12.0; C$_{31}$H$_{32}$N$_6$O$_9$ 3H$_2$O requires C, 54.2; H, 5.5; N, 12.2%.

EXAMPLE 16

Using analogous procedures to those described in the second and third paragraphs of Example 12, pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino|benzoate was reacted with methyl (2S)-2-amino-4-(tetrazol-5-yl)butyrate to give methyl (2S)-2-{o-fluoro-p-[N-methyl-N-((6RS)-2-methyl-3-pivaloyloxymethyl-4-oxo-3,4,7,8-tetrahydro-6H-cyclopenta[g]quinazolin-6-yl)amino]benzamido}-4-(tetrazol-5-yl)butyrate in 73% yield which in turn was hydrolysed with aqueous sodium hydroxide solution to give (2S)-2-{o-fluoro-p-[N-methyl-N-((6RS)-2-methyl-4-oxo-3,4,7,8-tetrahydro-6H-cyclopenta[g]quinazolin-6-yl)amino]benzamido}-4-(tetrazol-5-yl)butyric acid in 81% yield, m.p. 203°–205° C.;

NMR Spectrum: (CD$_3$SOCD$_3$) 2.2 (m, 4H), 2.32 (s, 3H), 2.68 (s, 3H), 3.02 (m, 4H), 4.45 (2 d's, 1H), 5.77 (t, 1H), 6.8 (d, 1H), 6.88 (d, 1H), 7.48 (s, 1H), 7.62 (d, 1H), 7.7 (s, 1H), 7.95 (t, 1H), 12.1 (broad s, 1H);

Elemental Analysis: Found C, 54.6; H, 5.1; N, 20.2; C$_{25}$H$_{25}$FN$_8$O$_4$ 1.5H$_2$O requires C, 54.8; H, 5.1; N, 20.4%.

The pentafluorophenyl o-fluoro-p-[N-methyl-N-((6RS)-2-methyl-4-oxo-3-pivaloyloxymethyl-3,4,7,8-tetrahydro-6H-cyclopenta[g]quinazolin-6-yl)amino]benzoate used as a starting material was obtained as follows:

An aqueous solution of formaldehyde (37% weight/volume, 17.55 ml) was added dropwise during 15 minutes to a stirred solution of pentafluorophenyl o-fluoro-p-[N-((6RS)-2-methyl-4-oxo-3-pivaloyloxymethyl-3,4,7,8-tetrahydro-6H-cyclopenta[g]quinazolin-6-yl)-amino]benzoate (13 g) in glacial acetic acid (100 ml). The mixture was stirred at ambient temperature for 1 hour. Sodium cyanoborohydride (1.36 g) was added portionwise during 30 minutes and the resultant mixture was stirred at ambient temperature for 2 hours. The mixture was poured onto a mixture of ice and water (500 ml) and extracted with ethyl acetate. The organic phase was dried (MgSO$_4$) and evaporated. The product was purified by column chromatography using increasingly polar mixtures of hexane and ethyl acetate as eluent. There was thus obtained the required starting material (11 g);

NMR Spectrum: (CDCl$_3$) 1.23 (s, 9H), 2.15 (m, 1H), 2.55 (m, 1H), 2.65 (s, 3H), 2.8 (s, 3H), 3.15 (m, 2H), 5.65 (t, 1H), 6.1 (2 d's, 2H), 6.6 (2 d's, 1H), 6.72 (2 d's, 1H), 7.53 (s, 1H), 7.97 (d, 1H), 8.03 (s, 1H).

EXAMPLE 17

A mixture of pentafluorophenyl p-[N-((6RS)-2-methyl-4-oxo-3,4,7,8-tetrahydro-6H-cyclopenta[g]quinazolin-6-yl)-N-(prop-2-ynyl)-amino|benzoate (0.1 g), tri-tert-butyl L-γ-glutamyl-D-glutamate (0.165 g), N-hydroxybenzotriazole (0.01 g), triethylamine (0.27 ml) and DMA (10 ml) was stirred at ambient temperature for 18 hours. The mixture was evaporated and the residue was partitioned between ethyl acetate and water. The organic phase was dried (MgSO$_4$) and evaporated. The residue was purified by column chromatography using initially ethyl acetate and then a 9:1 mixture of ethyl acetate and methanol as eluent. There was thus obtained tri-tert-butyl N-{p-[N-((6RS)-2-methyl-4-oxo-3,4,7,8-tetrahydro-6H-cyclopenta[g]quinazolin-6-yl)-N-(prop-2-ynyl)amino|benzoyl)-L-γ-glutamyl-D-glutamate as a gum (0.22 g);

NMR Spectrum: (CDCl$_3$) 1.45 (s, 27H), 1.7 (m, 4H), 2.2 (t, 1H), 2.3 (m, 4H), 2.52 (s, 3H), 2.55 (m, 1H), 3.0 (m, 1H), 3.25 (m, 1H), 3.36 (2 d's, 1H), 3.82 (2 d's, 1H), 4.02 (2 d's, 1H), 4.49 (m, 1H), 4.75 (m, 1H), 5.65 (t, 1H), 6.65 (d, 1H), 7.0 (d, 2H), 7.09 (t, 1H), 7.58 (s, 1H), 7.81 (d, 2H), 8.1 (s, 1H).

A mixture of the product so obtained, trifluoroacetic acid (2 ml) and methylene chloride (20 ml) was stirred at ambient temperature for 16 hours. The mixture was evaporated and the residue was dissolved in a saturated aqueous sodium bicarbonate solution (20 ml). The solution was acidified to pH4 by the addition of 2N aqueous hydrochloric acid. The precipitate was isolated, washed with water and dried under vacuum. There was thus obtained N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-γ-glutamyl-D-glutamic acid (0.066 g), m.p. 184° C.;

NMR Spectrum: (CD$_3$SOCD$_3$) 2.0 (m, 4H), 2.3 (m, 5H), 2.35 (s, 3H), 2.55 (m, 1H), 3.0 (s, 1H), 3.05 (m, 1H), 3.2 (m, 1H), 3.85 (d, 1H), 4.1 (d, 1H), 4.25 (2 d's, 1H), 4.4 (2 d's, 1H), 5.75 (t, 1H), 7.05 (d, 2H), 7.5 (s, 1H), 7.82 (d, 2H), 7.85 (s, 1H), 8.12 (d, 1H), 8.32 (d, 1H), 12.05 (s, 1H), 12.4 (broad s, 1H);

Elemental Analysis: Found C, 55.9; H, 5.4; N, 10.0; C$_{32}$H$_{33}$N$_5$O$_9$ 3H$_2$O requires C, 56.0; H, 5.6; N, 10.2%.

EXAMPLE 18

A mixture of p-[N-((6S)-2-methyl-4-oxo-3,4,7,8-tetrahydro-6H-cyclopenta[g]quinazolin-6-yl)-N-(prop-2-ynyl)amino]benzoic acid (4.6 g), methyl (2S)-2-amino-4-(tetrazol-5-yl)butyrate (3 g), N-hydroxybenzotriazole (0.1 g), N,N-dicyclohexylcarbodiimide (3.3 g) and DMA (200 ml) was stirred and heated to 50° C. for 10 hours. The mixture was evaporated and the residue was partitioned between ethyl acetate and a saturated aqueous sodium bicarbonate solution. The aqueous layer was acidified to pH4 by the addition of dilute hydrochloric acid. The precipitate was isolated, washed with water and dried. The product so obtained was purified by column chromatography using initially a 4:1 mixture of methylene chloride and methanol and then a 4:1:0.05 mixture of methylene chloride, methanol and acetic acid as eluent. There was thus obtained methyl (2S)-2-{p-|N-((6S)-2-methyl-4-oxo-3,4,7,8-tetrahydro-6H-cyclopental[g]quinazolin-6-yl)-N-(prop-2-ynyl)amino|benzamido}-4-(tetrazol-5-yl)butyrate (2.4 g).

A mixture of the butyrate so obtained, 1N aqueous sodium hydroxide solution (60 ml) and methanol (200 ml) was stirred at ambient temperature for 48 hours. The mixture was evaporated. Water (100 ml) was added to the residue and the mixture was acidified to pH4 by the addition of 2N aqueous hydrochloric acid. The precipitate was isolated by centrifugation and dried. The material so obtained was purified by column chromatography using initially a 4:1 mixture of methylene chloride and methanol and then a 4:1:0.005 mixture of methylene chloride, methanol and acetic acid as eluent. There was thus obtained (2S)-2-{p-|N-((6S)-2-methyl-4-oxo-3,4,7,8-tetrahydro-6H-cyclopenta[g]quinazolin-6-yl)-N-(prop-2-ynyl)amino|benzamido}-4-(tetrazol-5-yl)butyric acid (1.39 g), m.p. 224° C.;

NMR Spectrum: (CD$_3$SOCD$_3$) 2.25 (m, 3H), 2.35 (s, 3H), 2.5 (m, 1H), 2.99 (m, 3H), 3.1 (s, 1H), 3.15 (m, 1H), 3.85 (2 d's, 1H), 4.1 (m, 1H), 4.4 (m, 1H), 5.75 (t, 1H), 7.05 (d, 2H), 7.5 (s, 1H), 7.79 (s, 1H), 7.82 (d, 2H), 8.4 (d, 1H), 12.1 (broad s, 1H);

Elemental Analysis: Found C, 58.3; H, 5.1; N, 19.7; C$_{27}$H$_{26}$N$_8$O$_4$ 1.25H$_2$O 0.25CH$_3$CO$_2$H requires C, 58.4; H, 5.2; N, 19.8%.

EXAMPLE 19

Using analogous procedures to those described in Example 12, o-fluoro-p-|N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoic acid was reacted with pentafluorophenyl trifluoroacetate to give the pentafluorophenyl benzoate in 75% yield, which was in turn reacted with methyl (2S)-2-amino-4-(tetrazol-5-yl)butyrate to give methyl (2S)-2-{o-fluoro-p-[N-((6RS)-2-methyl-4-oxo-3-pivaloyloxymethyl-3,4,7,8-tetrahydro-6H-cyclopenta[g]quinazolin-6-yl)-N-(prop-2-ynyl)amino|benzamido}-4-(tetrazol-5-yl)butyrate in 87% yield, and which in turn was hydrolysed with aqueous sodium hydroxide solution to give (2S)-2-{o-fluoro-p-[N-((6RS)-2-methyl-4-oxo-3,4,7,8-tetrahydro- 6H-cyclopenta[g]quinazolin-6-yl)-N-(prop-2-ynyl)amino|benzamido}-4-(tetrazol-5-yl)butyric acid in 66% yield;

NMR Spectrum: (CD$_3$SOCD$_3$) 2.15–2.33 (s & m, 6H), 3.0 (t, 4H), 3.97 (m, 2H), 4.48 (m, 1H), 5.75 (t, 1H), 6.85 (t, 2H), 7.48 (s, 1H, 7.6 (t, 1H), 7.77 (s, 1H), 8.06 (t, 1H);

Elemental Analysis: Found C, 53.0; H, 4.5; N, 18.0; C$_{27}$H$_{25}$ FN$_8$O$_4$ 1H$_2$O 0.9NaCl requires C, 52.7; H, 4.4; N, 18.2%.

The o-fluoro-p-|N-((6RS)-2-methyl-4-oxo-3-pivaloyloxymethyl-3,4,7,8-tetrahydro-6H-cyclopenta[g]quinazolin-6-yl)-N-(prop-2-ynyl)amino]benzoic acid used as a starting material was obtained as follows:

A solution of 6-bromo-2-methyl-3-pivaloyloxymethyl-3,4,7,8-tetrahydro-6H-cyclopental[g]quinazolin-4-one (2.4 g) in DMA (15 ml) was added to a stirred mixture of p-amino-o-fluoro-β,β-dimethylstyrene (2.03 g), calcium carbonate (2.7 g) and DMA (25 ml) which had been heated to 70° C. The mixture was stirred at 70° C. for 1 hour. The mixture was cooled to ambient temperature and partitioned between ethyl acetate and water. The organic phase was washed with water, dried (MgSO$_4$) and evaporated. The residue was purified by column chromatography using increasingly polar mixtures of hexane and ethyl acetate as eluent. There was thus obtained o-fluoro-p-|N-((6RS)-2-methyl-4-oxo-3-pivaloyloxymethyl-3,4,7,8-tetrahydro-6H-cyclopenta|g| quinazolin-6-yl)amino|-β,β-dimethylstyrene (1.4 g);

NMR Spectrum: (CDCl$_3$) 1.23 (s, 9H), 1.81 (s, 3H), 1.91 (s, 3H), 1.95 (m, 1H), 2.64 (s, 3H), 2.70 (m, 1H), 3.06 (m, 2H), 4.05 (broad s, 1H), 5.03 (s, 1H), 6.1 (m, 3H), 6.42 (m, 2H), 7.06 (m, 1H), 7.48 (s, 1H), 8.24 (s, 1H).

A mixture of the product so obtained, propargyl bromide (6.1 g), calcium carbonate (0.88 g) and DHA (20 ml) was stirred and heated to 80° C. for 6 hours. The mixture was evaporated and the residue was partitioned between ethyl acetate and water. The organic phase was washed with water and with brine, dried (MgSO$_4$) and evaporated. The residue was purified by column chromatography using initially increasingly polar mixtures of hexane and ethyl acetate and then increasingly polar mixtures of methylene chloride and ethyl acetate as eluent. There was thus obtained o-fluoro-p-|N-((6RS)-2-methyl-4-oxo- 3-pivaloyloxymethyl-3,4,7,8-tetrahydro-6H-cyclopenta|g|quinazolin-6-yl)-N-(prop-2-ynyl)amino]-β,β-dimethylstyrene (1.04 g);

NMR Spectrum: (CDCl$_3$) 1.23 (s, 9H), 1.81 (s, 3H), 1.91 (s, 3H), 2.2 (t, 1H), 2.28–2.6 (m, 2H), 2.65 (s, 3H), 2.9–3.3 (m, 2H), 4.35 (2 d's, 2H), 5.5 (t, 1H), 6.1 (s, 2H), 6.16 (s, 1H), 6.66 (m, 2H), 7.13 (t, 1H), 7.5 (s, 1H), 8.13 (s, 1H).

A portion (0.626 g) of the material so obtained was dissolved in a mixture of methylene chloride (2 ml) and ethanol (250 ml). The mixture was cooled to –70° C. and ozone gas was passed into the solution for 7.5 minutes. Argon gas was bubbled into the solution for 5 minutes. Dimethyl sulphide (4 ml) was added and the mixture was allowed to warm to ambient temperature. The mixture was evaporated and the residue was purified by column chromatography using a 1:1 mixture of hexane and ethyl acetate as eluent. There was thus obtained o-fluoro-p-|N-((6RS)-2-methyl-4-oxo-3-pivaloyloxymethyl-3,4,7,8-tetrahydro-6H-cyclopentalquinazolin-6-yl)-N-(prop-2-ynyl)amino| benzaldehyde (0.47 g);

NMR Spectrum: (CDCl$_3$) 1.2 (s, 9H), 2.25 (m, 2H), 2.64 (m, 4H), 2.95–3.35 (m, 2H), 3.9 (m, 2H), 5.6 (t, 1H), 6.1 (s, 2H), 6.65 (m, 1H), 6.8 (m, 1H), 7.53 (s, 1H), 7.8 (t, 1H), 8.1 (s, 1H), 10.15 (s, 1H).

Sodium chlorite (0.28 g) and sulphamic acid (0.24 g) were added portionwise to a stirred mixture of the benzaldehyde so obtained, 0.2M sodium acetate in acetic acid buffer (pH4, 70 ml) and tert-butanol (70 ml). The mixture was stirred at ambient temperature for 24 hours. The mixture was partitioned between methylene chloride and a saturated aqueous sodium dihydrogen phosphate solution. The organic phase was washed with brine, dried (MgSO$_4$) and evaporated. The residue was purified by column chromatography to give o-fluoro-p-[N-((6RS)-2-methyl-4-oxo-3-pivaloyloxymethyl-3,4,7,8-tetrahydro-6H-cyclopenta[g] quinazolin-6-yl)-N-(prop-2-ynyl)amino]benzoic acid (0.41 g);

NMR Spectrum: (CDCl$_3$+CD$_3$SOCD$_3$) 1.2 (s, 9H), 2.33 (m, 2H), 2.63 (m, 4H), 2.97–3.3 (m, 2H), 4.3 (m, 2H), 5.6 (t, 1H), 6.1 (s, 2H), 6.72 (m, 2H), 7.52 (s, 1H), 7.86 (t, 1H), 8.05 (s, 1H).

The p-amino-o-fluoro-β,β-dimethylstyrene used in the preparation of the starting material above was obtained as follows.

A mixture of o-fluoro-p-nitrobenzaldehyde (3.35 g) and (2-methoxycarbonylprop-2-yl)triphenylphosphonium iodide (*Synth. Comm.*, 1982, 469: 11 g) was stirred and heated to 130° C. for 20 minutes. The mixture was cooled to ambient temperature and purified by column chromatography using a 100:1 mixture of hexane and diethyl ether as eluent. There was thus obtained o-fluoro-p-nitro-β,β-dimethylstyrene as an oil (3.05 g);

NMR Spectrum: (CDCl$_3$) 1.84 (s, 3H), 1.78 (s, 3H), 6.25 (s, 1H), 7.4 (t, 1H), 7.96 (m, 2H).

A portion (2.2 g) of the material so obtained was added to a stirred mixture of stannous chloride dihydrate (12.8 g) and ethyl acetate (200 ml) which had been heated to 50° C. The resultant mixture was stirred and heated to 70° C. for 1.5 hours. The mixture was cooled to ambient temperature and poured into a dilute aqueous ammonium hydroxide solution. The mixture was extracted with ethyl acetate. The organic phase was washed with water and with brine, dried (MgSO$_4$) and evaporated. There was thus obtained p-amino-o-fluoro-β,β-dimethylstyrene as an oil (1.85 g);

NMR Spectrum: (CDCl$_3$) 1.76 (s, 3H), 1.85 (s, 3H), 3.7 (broad s, 2H), 6.13 (s, 1H), 6.38 (m, 2H), 7.0 (t, 1H).

EXAMPLE 20

Using analogous procedures to those described in Example 12, o-fluoro-p-|N-((6RS)-2-methyl-4-oxo-3-pivaloyloxymethyl-3,4,7,8-tetrahydro-6H-cyclopental|g| quinazolin-6-yl)-N-(prop-2-ynyl)amino|benzoic acid was reacted with pentafluorophenyl trifluoroacetate to give the pentafluorophenyl benzoate in 75% yield, which was in turn reacted with diethyl L-glutamate to give diethyl N-{o-fluoro-p-[N-((6RS)-2-methyl-4-oxo-3-pivaloyloxymethyl-3,4,7,8-tetrahydro-6H-cyclopenta[g]-quinazolin-6-yl)-N-(prop-2-ynyl)amino|benzoyl}-L-glutamate in 79% yield, and which in turn was hydrolysed with aqueous sodium hydroxide to give N-{o-fluoro-p-[N-((6RS)-2-methyl-4-oxo-3,4,7,8-tetrahydro-6H-cyclopenta[g]quinazolin-6-yl)-N-(prop-2-ynyl)amino|benzoyl-L-glutamic acid in 56% yield;

NMR Spectrum: (CD$_3$SOCD$_3$) 1.86–3.35 (m, 8H), 3.98 (m, 2H), 4.41 (m, 1H), 5.75 (t, 1H), 6.84 (m, 2H), 7.48 (s, 1H), 7.6 (m, 2H), 7.93 (t, 1H), 12.2 (broad s, 1H);

Elemental Analysis: Found C, 59.4; H, 5.0; N, 10.0; C$_{27}$H$_{25}$FN$_4$O$_6$ 0.5H$_2$O 0.3NaCl requires C, 59.3; H, 4.8; N, 10.2%.

EXAMPLE 21

A mixture of pentafluorophenyl p-[N-((6S)-2-methyl-4-oxo-3,4,7,8-tetrahydro-6H-cyclopenta[g]quinazolin-6-yl)-N-(prop-2-ynyl)amino]benzoate (0.1 g), m-nitrobenzylamine hydrochloride (0.152 g) 1,1'-carbonyldi-imidazole (0.065 g), triethylamine (0.12 ml) and DMA (20 ml) was stirred at ambient temperature for 24 hours. The mixture was evaporated and the residue was partitioned between ethyl acetate and water. The organic phase was dried (MgSO$_4$) and evaporated. The residue was purified by column chromatography using initially ethyl acetate and then a 19:1 mixture of methylene chloride and methanol as eluent. There was thus obtained p-[N-((6S)-2-methyl-4-oxo-3,4,7,8-tetrahydro-6H-cyclopenta[g] quinazolin-6-yl)-N-(prop-2-ynyl)amino]-N-(m-nitrobenzyl) benzamide (0.06 g), m.p. 169°–171° C.;

NMR Spectrum: (CD$_3$SOCD$_3$) 2.2 (m, 1H), 2.33 (s, 3H), 2.5 (m, 1H), 3.0 (m, 1H), 3.1 (t, 1H), 3.2 (m, 1H), 3.85 (2 d's, 1H), 4.1 (2 d's, 1H), 4.6 (d, 2H), 5.75 (t, 1H), 7.05 (d, 2H), 7.5 (s, 1H), 7.62 (t, 1H), 7.77 (d, 1H), 7.8 (s, 1H), 7.82 (d, 2H), 8.1 (2 d's, 1H), 8.18 (d, 1H), 8.88 (t, 1H), 12.1 (broad s, 1H);

Elemental Analysis: Found C, 66.6; H, 5.3; N, 12.7; C$_{29}$H$_{25}$N$_5$O$_4$ 1H$_2$O requires C, 66.2; H, 5.1; N, 13.3%.

EXAMPLE 22

Using an analogous procedure to that described in the first paragraph of Example 3, p-|N-((6R)-2-methyl-4-oxo-3,4,7,8-tetrahydro-6H-cyclopenta|g|quinazolin-6-yl)-N-(prop-2-ynyl)amino|benzoic acid was reacted with pentafluorophenol to give pentafluorophenyl p-|N-((6R)-2-methyl-4-oxo-3,4,7,8-tetrahydro-6H-cyclopenta|g|quinazolin-6-yl)-N-(prop-2-ynyl)amino|benzoate in 68% yield.

A mixture of the material so obtained (0.1 g), m-nitrobenzylamine hydrochloride (0.14 g), N-hydroxybenzotriazole (0.01 g), triethylamine (0.54 ml) and DMA (10 ml) was stirred at ambient temperature for 18 hours. The mixture was evaporated and the residue was partitioned between methylene chloride (20 ml) and water (20 ml). Insoluble material was isolated and dried. The organic phase was dried (MgSO$_4$) and evaporated. The residue and the insoluble material were combined and triturated under diethyl ether. There was thus obtained p-|N-((6R)-2-methyl-4-oxo-3,4,7,8-tetrahydro-6H-cyclopenta[g|quinazolin-6-yl)-N-(prop-2-ynyl)amino]-N-(m-nitrobenzyl)benzamide (0.075 g), m.p. 157°–159° C.;

NMR Spectrum: (CD$_3$SOCD$_3$) 2.2 (m, 1H), 2.33 (s, 3H), 2.5 (m, 1H), 3.0 (m, 1H), 3.1 (t, 1H), 3.2 (m, 1H), 3.85 (d, 1H), 4.1 (d, 1H), 4.6 (d, 2H), 5.75 (t, 1H), 7.05 (d, 2H), 7.5 (s, 1H), 7.62 (t, 1H), 7.77 (d, 1H), 7.8 (s, 1H), 7.82 (d, 2H), 8.1 (2 d's, 1H), 8.18 (d, 1H), 8.88 (t, 1H), 12.2 (broad s, 1H);

Elemental Analysis: Found C, 62.3; H, 5.1; N, 12.2; C$_{29}$H$_{25}$N$_5$O$_4$ 3H$_2$O requires C, 62.0; H, 5.5; N, 12.5%.

EXAMPLE 23

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur. | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur. | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 mg |
| Lactose Ph.Eur. | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid | |
| (to adjust pH to 7.6) | |
| Polyethylene glycol 400 | 4.5% w/v |
| Water for injection to 100% | |

| | | |
|---|---|---|
| (f) | Injection II | (10 mg/ml) |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

The above formulations may be obtained by conventional procedures well known in the pharmaceutical art. The tablets (a) to (c) may be enteric coated by conventional means, for example to provide a coating of cellulose acetate phthalate.

We claim:

1. A tricyclic compound of the formula I

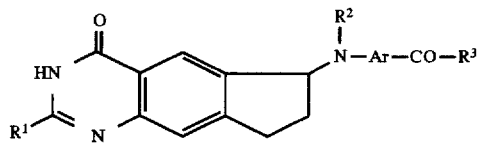

wherein $R^1$ is hydrogen, amino, (1–4C)alkyl, (1–4C)alkoxy, hydroxy-(1–4C)alkyl or fluoro-(1–4C)alkyl;

$R^2$ is hydrogen, (1–4C)alkyl, (3–4C)alkenyl, (3–4C) alkynyl, hydroxy-(2–4C)alkyl, halogeno-(2–4C)alkyl or cyano-(1–4C)alkyl;

Ar is phenylene, thiophenediyl, thiazolediyl, pyridinediyl or pyrimidinediyl which may optionally bear one or two substituents selected from the group consisting of halogeno, hydroxy, amino, nitro, cyano, trifluoromethyl, (1–4C)alkyl and (1–4C)alkoxy; and $R^3$ is a group of the formula

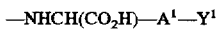
—NHCH(CO₂H)—A¹—Y¹ wherein $A^1$ is (1–6C)alkylene and $Y^1$ is carboxy, tetrazol-5-yl, N-[(1–4C)alkylsulphonyl]carbamoyl, N-(phenylsulphonyl)carbamoyl, tetrazol-5-ylthio, tetrazol-5-ylsulphinyl or tetrazol-5-ylsulphonyl, or $Y^1$ is a group of the formula

—CONH—CH(CO₂H)—A²—Y² wherein the α-amino acid carbon atom has the D-configuration, $A^2$ is (1–6C)alkylene and $Y^2$ is carboxy or tetrazol-5-yl, and wherein said N-(phenylsulphonyl) carbamoyl group may optionally bear one or two substituents on the phenyl ring selected from the group consisting of halogeno, nitro, (1–4C)alkyl and (1–4C)alkoxy, or $R^3$ is a N-linked naturally-occurring amino acid selected from the group consisting of L-alanine, L-leucine, L-isoleucine, L-valine and L-phenylalanine, or $R^3$ is a group of the formula

—NH—A³—Y³ wherein $A^3$ is (1–3C)alkylene and $Y^3$ is phenyl which may optionally bear one, two or three substituents selected from the group consisting of halogeno, hydroxy, amino, nitro, cyano, trifluoromethyl, (1–4C)alkyl and (1–4C)alkoxy;

or a pharmaceutically-acceptable salt or ester thereof.

2. A tricyclic compound of the formula I as claimed in claim 1 wherein $R^1$ is amino or methyl;

$R^2$ is prop-2-ynyl;

Ar is 1,4-phenylene which may optionally bear one or two fluoro or chloro substituents, or Ar is thiophene-2,5-diyl or thiazole-2,5-diyl (with the —CO— group in the 2-position); and $R^3$ is a group of the formula

—NHCH(CO₂H)—A¹—Y¹ wherein $A^1$ is methylene, ethylene, trimethylene, tetramethylene or pentamethylene and $Y^1$ is carboxy, tetrazol-5-yl, N-methylsulphonylcarbamoyl or tetrazol-5-ylthio;

or $R^3$ is a group of the formula

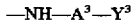
—NH—A³—Y³ wherein $A^3$ is methylene or ethylene and $Y^3$ is phenyl which may optionally bear one or two substituents selected from the group consisting of fluoro, chloro, nitro, cyano and trifluoromethyl; or a pharmaceutically-acceptable salt or ester thereof.

3. A tricyclic compound of the formula I as claimed in claim 1 wherein $R^1$ is methyl;

$R^2$ is hydrogen, methyl, ethyl, propyl, prop-2-enyl or prop-2-ynyl;

Ar is 1,4-phenylene or 2-fluoro-1,4-phenylene (with the —CO— group in the 1-position), or Ar is pyridine-2, 5-diyl (with the —CO— group in the 2-position); and $R^3$ is a group of the formula

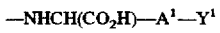
—NHCH(CO₂H)—A¹—Y¹ wherein $A^1$ is ethylene, trimethylene, tetramethylene or pentamethylene and $Y^1$ is carboxy, tetrazol-5-yl, N-methylsulphonylcarbamoyl or tetrazol-5-ylthio; or a pharmaceutically-acceptable salt or ester thereof.

4. A tricyclic compound of the formula I as claimed in claim 1 wherein $R^1$ is methyl;

$R^2$ is prop-2-ynyl;

Ar is 1,4-phenylene or 2-fluoro-1,4-phenylene (with the —CO— group in the 1-position), or Ar is pyridine-2, 5-diyl (with the —CO— group in the 2-position); and $R^3$ is a group of the formula

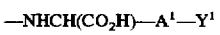
—NHCH(CO₂H)—A¹—Y¹ wherein $A^1$ is ethylene and $Y^1$ is carboxy or tetrazol-5-yl; or a pharmaceutically-acceptable salt or ester thereof.

5. A tricyclic compound of the formula I as claimed in claim 1 selected from

N-{p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid, (2S)-2-{p-[N-((6RS)-2-methyl-4-oxo-3,4,7,8-tetrahydro-6H-cyclopenta[g]quinazolin-6-yl)-N-(prop-2-ynyl)amino]benzamido}adipic acid, (2S)-2-{p-[N-((6RS)-2-methyl-4-oxo-3,4,7,8-tetrahydro-6H-cyclopenta[g]quinazolin-6-yl)-N-(prop-2-ynyl)amino]benzamido}pimelic acid, (2S)-2-{p-[N-((6RS)-2-methyl-4-oxo-3,4,7,8-tetrahydro-6H-cyclopenta[g]quinazolin-6-yl)-N-(prop-2-ynyl)amino]benzamido}-5-[(N-methylsulphonyl)carbamoyl] pentanoic acid, 2-{p-[N-((6S)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyric acid and (2R)-2-{p-[N-((6RS)-2-methyl-4-oxo-3,4,7,8-tetrahydro-6H-cyclopenta[g]quinazolin-6-yl)-N-(prop-2-ynyl)amino]benzamido}-3-(tetrazol-5-ylthio)propionic acid;

or a pharmaceutically-acceptable salt or ester thereof.

6. A tricyclic compound of the formula I as claimed in claim 1 selected from:

(2S)-2-{p-[N-((6S)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyric acid, (2S)-2-{5-[N-((6RS)-2-methyl-4-oxo-3,4,7,8-tetrahydro-6H-cyclopenta[g]quinazolin-6-yl)-N-(prop-2-ynyl)amino]pyridine-2-carboxamido}-4-(tetrazol-5-yl)butyric acid, (2S)-2-{o-fluoro-p-[N-methyl-N-((6RS)-2-methyl-4-oxo-3,4,7,8-tetrahydro-6H-cyclopenta[g]quinazolin-6-yl)amino]benzamido}-4-(tetrazol-5-yl)butyric acid, (2S)-2-{o-fluoro-p-[N-((6RS)-2-methyl-4-oxo-3,4,7,8-tetrahydro-6H-cyclopenta[g]quinazolin-6-yl)-N-(prop-2-ynyl)amino]benzamido}-4-(tetrazol-5-yl)butyric acid and N-{o-fluoro-p-[N-((6RS)-2-methyl-4-oxo-3,4,7,8-tetrahydro-6H-cyclopenta[g]quinazolin-6-yl)-N-(prop-2-ynyl)amino]benzoyl}-L-glutamic acid;

or a pharmaceutically-acceptable salt or ester thereof.

7. A tricyclic compound of the formula I as claimed in claim 1 being:

N-(3-cyanobenzyl)-p-[N-((6RS)-2-methyl-4-oxo-3,4,7,8-tetrahydro-6H-cyclopenta[g]quinazolin-6-yl)-N-(prop-2-ynyl)amino]benzamide;

or a pharmaceutically-acceptable salt thereof.

8. A pharmaceutical composition which comprises a tricyclic compound of the formula I, or a pharmaceutically-acceptable salt or ester thereof, as claimed in any one of claims 1 to 7 in association with a pharmaceutically-acceptable diluent or carrier.

9. A process for the preparation of a tricyclic derivative of the formula I,

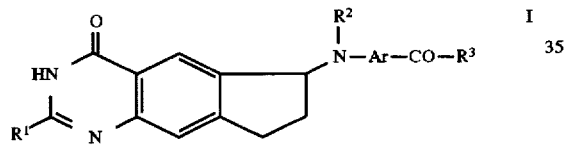

wherein $R^1$ is hydrogen, amino, (1–4C)alkyl, (1–4C)alkoxy, hydroxy-(1–4C)alkyl or fluoro-(1–4C)alkyl;

$R^2$ is hydrogen, (1–4C)alkyl, (3–4C)alkenyl, (3–4C)alkynyl, hydroxy-(2–4C)alkyl, halogeno-(2–4C)alkyl or cyano-(1–4C)alkyl;

Ar is phenylene, thiophenediyl, thiazolediyl, pyridinediyl or pyrimidinediyl which may optionally bear one or two substituents selected from the group consisting of halogeno, hydroxy, amino, nitro, cyano, trifluoromethyl, (1–4C)alkyl and (1–4C)alkoxy; and $R^3$ is a group of the formula

—NHCH(CO$_2$H)—A$^1$—Y$^1$ wherein $A^1$ is (1–6C)alkylene and $Y^1$ is carboxy, tetrazol-5-yl, N-[(1–4C)alkylsulphonyl]carbamoyl, N-phenylsulphonyl)carbamoyl, tetrazol-5-ylthio, tetrazol-5-ylsulphinyl or tetrazol-5-ylsulphonyl, or $Y^1$ is a group of the formula

—CONH—CH (CO$_2$H)—A$^2$—Y$^2$ wherein the α-amino acid carbon atom has the D-configuration, $A^2$ is (1–6C)alkylene and $Y^2$ is carboxy or tetrazol-5-yl, and wherein said N-(phenylsulphonyl)carbamoyl group may optionally bear one or two substituents on the phenyl ring selected from the group consisting of halogeno, nitro, (1–4C)alkyl and (1–4C) alkoxy, or $R^3$ is a N-linked naturally-occurring amino acid selected from the group consisting of L-alanine, L-leucine, L-isoleucine, L-valine and L-phenylalanine, or $R^3$ is a group of the formula

—NH—A$^3$—Y$^3$ wherein $A^3$ is (1–3C)alkylene and $Y^3$ is phenyl which may optionally bear one, two or three substituents selected from the group consisting of halogeno, hydroxy, amino, nitro, cyano, trifluoromethyl, (1–4C)alkyl and (1–4C)alkoxy;

or a pharmaceutically-acceptable salt or ester thereof, which process comprises the reaction of an acid of the formula II

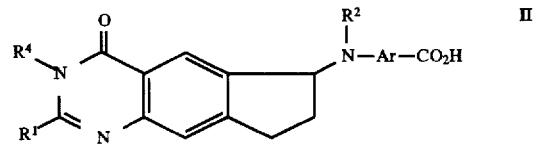

or a reactive derivative thereof, wherein $R^4$ is hydrogen or a protecting group, with the amino group of a compound of the formula $R^3$—H.

10. The process of claim 9 wherein said tricyclic derivative is prepared in the form of a pharmaceutically-acceptable salt, said process additionally comprising reacting the compound of formula I with an acid or base to form said pharmaceutically-acceptable salt.

11. The process of claim 9 wherein said tricyclic derivative is prepared in the form of a pharmaceutically-acceptable ester, said process additionally comprising reacting the compound of formula I with a (1–6C)alcohol to form said pharmaceutically-acceptable ester.

* * * * *